(12) United States Patent
Miller et al.

(10) Patent No.: US 9,781,929 B2
(45) Date of Patent: Oct. 10, 2017

(54) BACTERIOPHAGE AND METHODS OF USING

(71) Applicants: Altria Client Services LLC, Richmond, VA (US); Micreos BV, Wageningen (NL)

(72) Inventors: Elisabeth Miller, Chesterfield, VA (US); Ujwala Warek, Chester, VA (US); Dongmei Xu, Glen Allen, VA (US); Fritz Eichenseher, Richmond, VA (US); Steven Hagens, Richmond, VA (US); Chengalrayan Kudithipudi, Midlothian, VA (US)

(73) Assignees: ALTRIA CLIENT SERVICES LLC, Richmond, VA (US); Micreos BV, Wageningen (NL)

( * ) Notice: Subject to any disclaimer, the term of this patent is extended or adjusted under 35 U.S.C. 154(b) by 0 days.

(21) Appl. No.: 15/009,926

(22) Filed: Jan. 29, 2016

(65) Prior Publication Data

US 2016/0219876 A1   Aug. 4, 2016

Related U.S. Application Data

(60) Provisional application No. 62/109,163, filed on Jan. 29, 2015.

(51) Int. Cl.
*A24B 15/20* (2006.01)
*C07K 14/005* (2006.01)
*C12N 7/00* (2006.01)
*A01N 37/18* (2006.01)
*A24B 15/18* (2006.01)
*A24B 15/24* (2006.01)
*A24B 15/30* (2006.01)

(52) U.S. Cl.
CPC ............ *A01N 37/18* (2013.01); *A24B 15/183* (2013.01); *A24B 15/20* (2013.01); *A24B 15/245* (2013.01); *A24B 15/30* (2013.01); *C07K 14/005* (2013.01); *C12N 7/00* (2013.01); *C12N 2795/00021* (2013.01); *C12N 2795/00022* (2013.01); *C12N 2795/00031* (2013.01)

(58) Field of Classification Search
CPC ........ A24B 15/20; C07K 14/005; C12N 7/00; C12N 15/8216; A01N 37/18; A01N 61/00
See application file for complete search history.

(56) References Cited

U.S. PATENT DOCUMENTS

| | | |
|---|---|---|
| 4,528,993 A | 7/1985 | Sensabaugh et al. |
| 4,660,577 A | 4/1987 | Sensabaugh et al. |
| 4,848,373 A | 7/1989 | Lenkey |
| 5,204,257 A | 4/1993 | DeBonville et al. |
| 5,372,149 A | 12/1994 | Roth et al. |
| 5,447,836 A | 9/1995 | Wolber et al. |
| 5,660,812 A | 8/1997 | Merril et al. |
| 5,688,501 A | 11/1997 | Merril et al. |
| 5,712,089 A | 1/1998 | Borrebaeck et al. |
| 5,723,330 A | 3/1998 | Rees et al. |
| 5,766,892 A | 6/1998 | Merril et al. |
| 5,811,093 A | 9/1998 | Merril et al. |
| 5,914,240 A | 6/1999 | Sanders |
| 5,958,675 A | 9/1999 | Wicks et al. |
| 6,027,930 A | 2/2000 | Borrebaeck et al. |
| 6,056,954 A | 5/2000 | Fischetti et al. |
| 6,090,541 A | 7/2000 | Wicks et al. |
| 6,121,036 A | 9/2000 | Ghanbari et al. |
| 6,190,856 B1 | 2/2001 | Li |
| 6,238,661 B1 | 5/2001 | Fischetti et al. |
| 6,248,324 B1 | 6/2001 | Fischetti et al. |
| 6,254,866 B1 | 7/2001 | Fischetti et al. |
| 6,264,945 B1 | 7/2001 | Fischetti et al. |
| 6,265,169 B1 | 7/2001 | Cortese et al. |
| 6,277,399 B1 | 8/2001 | Fischetti et al. |
| 6,326,002 B1 | 12/2001 | Fischetti et al. |
| 6,335,012 B1 | 1/2002 | Fischetti et al. |
| 6,395,504 B1 | 5/2002 | Trudil |
| 6,432,444 B1 | 8/2002 | Fischetti et al. |
| 6,436,661 B1 | 8/2002 | Adams et al. |
| 6,448,083 B1 | 9/2002 | Larocca et al. |
| 6,555,331 B1 | 4/2003 | Hyman et al. |
| 6,635,238 B2 | 10/2003 | Delisle |
| 6,685,937 B2 | 2/2004 | Fischetti et al. |
| 6,699,701 B1 | 3/2004 | Sulakvelidze et al. |
| 6,737,079 B2 | 5/2004 | Fischetti et al. |
| 6,759,229 B2 | 7/2004 | Schaak |
| 6,783,930 B1 | 8/2004 | Pelletier et al. |
| 6,896,882 B2 | 5/2005 | Ramachandran et al. |
| 6,919,075 B1 | 7/2005 | Soloman et al. |
| 6,936,244 B2 | 8/2005 | Fiochetti et al. |
| 6,942,858 B1 | 9/2005 | Ghanbari et al. |
| 6,955,893 B2 | 10/2005 | Delisle |

(Continued)

FOREIGN PATENT DOCUMENTS

| | | |
|---|---|---|
| WO | WO 2009/012481 | 1/2009 |
| WO | WO 2014/150870 | 9/2014 |

OTHER PUBLICATIONS

Schmelcher, M., et al., 2012. "Bacteriophage endolysins as novel antimicrobials." Future microbiology 7 (10): 1147-1171.*
Dorval-Couchesne et al., "Production and Application of Bacteriophage and Bacteriophage-Encoded Lysins," *Recent Patents on Biotechnology*, 2009, 3:37-45.
GenBank Accession No. EHR86787.1.
GenBank Accession No. YP_004149412.1.
GenBank Accession No. ZP_06751371.1.
Hawtrey et al., "Isolation, Characterization, and Annotation: The Search for Novel Bacteriophage Genomes," *The Journal of Experimental Secondary Science*, 2012, 1-9.
Hendrix et al., "Evolutionary relationships among diverse bacteriophages and prophages: all the world's a phage," *PNAS USA*, 1999, 96:2192-7.
International Preliminary Report on Patentability in International Application No. PCT/US2014/024432, mailed on Jul. 7, 2015, 10 pages.

(Continued)

*Primary Examiner* — Lee A Visone
*Assistant Examiner* — Weihua Fan
(74) *Attorney, Agent, or Firm* — Fish & Richardson P.C.

(57) ABSTRACT

Bacteriophage are provided, and methods of making and using the bacteriophage also are provided.

22 Claims, 13 Drawing Sheets

(56) References Cited

U.S. PATENT DOCUMENTS

| | | | |
|---|---|---|---|
| 7,063,837 B2 | 6/2006 | Fischetti et al. | |
| 7,087,226 B2 | 8/2006 | Ramachandran et al. | |
| 7,128,916 B2 | 10/2006 | March | |
| 7,141,241 B2 | 11/2006 | Fischetti et al. | |
| 7,169,408 B2 | 1/2007 | Fischetti et al. | |
| 7,244,612 B2 | 7/2007 | Goodridge | |
| 7,276,332 B2 | 10/2007 | Goodridge | |
| 7,332,307 B2 | 2/2008 | Carlton et al. | |
| 7,459,272 B2 | 12/2008 | Morris et al. | |
| 7,588,929 B2 | 9/2009 | Bujanover | |
| 7,632,637 B1 | 12/2009 | Boss et al. | |
| 7,687,069 B2 | 3/2010 | Fischetti et al. | |
| 7,694,686 B2 | 4/2010 | Atchley et al. | |
| 7,951,579 B2 | 5/2011 | Hargis et al. | |
| 7,985,573 B2 | 7/2011 | Yacoby et al. | |
| 8,003,323 B2 | 8/2011 | Morris et al. | |
| 8,092,990 B2 | 1/2012 | Voorhees | |
| 2004/0118422 A1 | 6/2004 | Lundin et al. | |
| 2005/0178398 A1 | 8/2005 | Breslin et al. | |
| 2005/0244521 A1 | 11/2005 | Strickland et al. | |
| 2006/0191548 A1 | 8/2006 | Strickland et al. | |
| 2009/0036307 A1* | 2/2009 | Gabriel ............. | C12N 15/8281 504/117 |
| 2010/0116281 A1 | 5/2010 | Marshall et al. | |
| 2010/0203180 A1 | 8/2010 | Yoon et al. | |
| 2012/0024301 A1 | 2/2012 | Carroll et al. | |
| 2012/0031414 A1 | 2/2012 | Atchley et al. | |
| 2012/0031416 A1 | 2/2012 | Atchley et al. | |

OTHER PUBLICATIONS

International Search Report and Written Opinion in International Application No. 2014/024432, mailed on Nov. 3, 2014, 18 pages.
Invitation to Pay Fees in International Application No. PCT/US2014/024432, mailed Sep. 15, 2014, 8 pages.
Invitation to Pay Fees in International Application No. PCT/US2016/015520, mailed Apr. 15, 2016, 7 pages.
Loessner et al., "C-terminal domains of Listeria monocytogenes bacteriophage murein hydrolases determine specific recognition and high-affinity binding to bacterial cell wall carbohydrates," Mol. Microbiol., 2002, 44:335-49.
Ozawa et al., "Bacteriophage P4282, a parasite of Ralstonia solanacearum, encodes a bacteriolytic protein important for lytic infection of its host," Molecular Genetics and Genomics, 2001, 265.1: 95-101.
Pope et al., "Expanding the Diversity of Mycobacteriophages: Insights into Genome Architecture and Evolution," *PLoS One*, Jan. 2011, 6(1):1-20.
Seeley and Primrose, "A Review: The isolation of bacteriophages from the environment," *J. Applied Bacteriology*, 1982, 53:1-17.
Son et al., "Antibacterial and biofilm removal activity of a podoviridae Staphylococcus aureus bacteriophage SAP-2 and a derived recombinant cell-wall-degrading enzyme," Applied Microbiology and Biotechnology, Dec. 2009, 86(5):1439-1449.
Takac, "Functional analysis of the lysis genes of *Staphylococcus aureus* phage P68 in *Escherichia coli*," Microbiology, Jul. 2005, 151(7):2331-2342.
Tanaka et al., "Control of tobacco bacterial wilt by an avirulent strain of Pseudomonas solanacearum M4S and its bacteriophage," Ann. Phytopath. Soc. Japan, Jan. 1990, 56:243-246.
Tso, "Seed to Smoke," Tobacco, Production, Chemistry and Technology, Davis & Nielsen, eds., 1999, Chapter 1, 33 pages.
Vybiral et al., "Complete nucleotide sequence and molecular characterization of two lytic *Staphylococcus aureus* phages: 44AHJD and P68," FEMS Microbiology Letters, Feb. 2003, 219(2):275-283.
Database accession No. AOAODOF4B8, Database UniProt [Online] Apr. 29, 2015, "Full=Phage N-acetylrnurarnoyl-L-alanine arnidase, (EC0:00003131EMBL:KI060252.1}; EC~3.5.1.28 {EC0:0000313!EMBL:KI060252.1)," retrieved from http://ibis/exam/dbfetch.jsp?id=UNIPROT:AOAODOF4B8, 1 page.
Jin et al., "Roles of bacteriophage GVE2 endolysin in host lysis at high temperatures," Microbiology, 2013, 159:1597-1605.
Schmelcher et al., "Bacteriophage endolysins as novel antimicrobials," Future Microbiology, 2012, 7(10):1147-1171.
International Search Report and Written Opinion in International Application No. PCT/US2016/015516, mailed Jun. 2, 2016, 14 pages.
International Search Report and Written Opinion in International Application No. PCT/US2016/015520, mailed Jun. 22, 2016, 16 pages.

* cited by examiner

US 9,781,929 B2

BACTERIOPHAGE AND METHODS OF USING

CROSS REFERENCE TO RELATED APPLICATIONS

This application claims benefit under 35 U.S.C. §119(e) to U.S. Application No. 62/109,163, filed Jan. 29, 2015.

TECHNICAL FIELD

This disclosure generally relates to bacteriophage.

BACKGROUND

Bacteriophage destroy bacteria but are harmless to humans. They are strain and, usually, species specific, and they are abundant in nature, in foods, and in the intestinal tract of animals. Bacteriophage are about 100 times smaller than bacteria, and they leave no ecological footprint. Bacteriophage are generally recognized as safe (GRAS).

The lytic lifecycle of bacteriophage typically includes adsorption to a bacterial cell, infection, which includes injecting their nucleic acid into the bacterial cell, replication, maturation, and assembly of bacteriophage inside the bacterial cell. The lytic lifecycle culminates in lysis of the bacterial cell to release the progeny bacteriophage.

SUMMARY

This disclosure describes bacteriophage, as well as methods of making and using such bacteriophage.

In one aspect, an isolated bacteriophage having lytic activity against Carnobacteriaceae is provided. Such a bacteriophage generally includes a nucleic acid sequence encoding an endolysin, wherein the nucleic acid sequence has at least 95% sequence identity to the nucleic acid sequence shown in SEQ ID NO:1. In some embodiments, the nucleic acid sequence has at least 99% sequence identity to the nucleic acid sequence shown in SEQ ID NO:1. In some embodiments, the nucleic acid sequence has the sequence shown in SEQ ID NO:1. In some embodiments, the endolysin encoded by the nucleic acid sequence has the amino acid sequence shown in SEQ ID NO:2.

In another aspect, an isolated bacteriophage having lytic activity against Carnobacteriaceae is provided. Such a bacteriophage generally includes a nucleic acid sequence encoding an endolysin having at least 95% sequence identity to the amino acid sequence shown in SEQ ID NO:2. In some embodiments, the endolysin has at least 99% sequence identity to the amino acid sequence shown in SEQ ID NO:2. In some embodiments, the endolysin has the amino acid sequence shown in SEQ ID NO:2.

In one aspect, an isolated nucleic acid molecule is provided. Such a nucleic acid molecule typically includes a nucleic acid sequence having at least 95% sequence identity to the nucleic acid sequence shown in SEQ ID NO:1. In some embodiments, the nucleic acid molecule comprises a nucleic acid sequence having at least 99% sequence identity to the nucleic acid sequence shown in SEQ ID NO:1. In some embodiments, the nucleic acid molecule comprises a nucleic acid sequence having the sequence shown in SEQ ID NO:1. In some embodiments, the nucleic acid molecule encodes a polypeptide having the amino acid sequence shown in SEQ ID NO:2.

In still another aspect, a vector comprising any of the isolated nucleic acids described herein is provided. In yet another aspect, a host cell comprising a vector as described herein is provided.

In another aspect, a purified polypeptide is provided. Such a polypeptide generally includes an amino acid sequence having at least 95% sequence identity to the amino acid sequence shown in SEQ ID NO:2. In some embodiments, the amino acid sequence has at least 99% sequence identity to the amino acid sequence shown in SEQ ID NO:2. In some embodiments, the amino acid sequence has the sequence shown in SEQ ID NO:2.

In one aspect, a method of making a polypeptide is provided. Such a method generally includes culturing a host cell as described herein under appropriate conditions.

In another aspect, a method for reducing the number of viable Carnobacteriaceae in tobacco is provided. Such a method typically includes contacting tobacco with an effective amount of a composition comprising an isolated bacteriophage as described herein, an isolated nucleic acid as described herein, a vector as described herein, a host cell as described herein, or a purified polypeptide as described herein. In some embodiments, the tobacco is contacted with the composition comprising the bacteriophage prior to fermentation of the tobacco. In some embodiments, the method reduces the level of TSNAs in the tobacco.

In one aspect, an isolated bacteriophage having lytic activity against *Virgibacillus* is provided. Such a bacteriophage generally includes a nucleic acid sequence encoding an endolysin, wherein the nucleic acid sequence has at least 95% sequence identity to the nucleic acid sequence shown in SEQ ID NO:3. In some embodiments, the nucleic acid sequence has at least 99% sequence identity to the nucleic acid sequence shown in SEQ ID NO:3. In some embodiments, the nucleic acid sequence has the sequence shown in SEQ ID NO:3. In some embodiments, the endolysin encoded by the nucleic acid sequence has the amino acid sequence shown in SEQ ID NO:4.

In another aspect, an isolated bacteriophage having lytic activity against *Virgibacillus* is provided. Such a bacteriophage generally includes a nucleic acid sequence encoding an endolysin having at least 95% sequence identity to the amino acid sequence shown in SEQ ID NO:4. In some embodiments, the endolysin has at least 99% sequence identity to the amino acid sequence shown in SEQ ID NO:4. In some embodiments, the endolysin has the amino acid sequence shown in SEQ ID NO:4.

In still another aspect, an isolated nucleic acid molecule is provided. Generally, the nucleic acid molecule includes a nucleic acid sequence having at least 95% sequence identity to the nucleic acid sequence shown in SEQ ID NO:3. In some embodiments, the nucleic acid molecule includes a nucleic acid sequence having at least 99% sequence identity to the nucleic acid sequence shown in SEQ ID NO:3. In some embodiments, the nucleic acid molecule comprises a nucleic acid sequence having the sequence shown in SEQ ID NO:3. In some embodiments, the nucleic acid molecule encodes a polypeptide having the amino acid sequence shown in SEQ ID NO:4.

In still another aspect, a vector that includes any of the isolated nucleic acids described herein is provided. In yet another aspect, a host cell that includes any of the vectors described herein is provided.

In another aspect, a purified polypeptide is provided. Typically, such a polypeptide includes an amino acid sequence having at least 95% sequence identity to the amino acid sequence shown in SEQ ID NO:4. In some embodiments, the amino acid sequence has at least 99% sequence identity to the amino acid sequence shown in SEQ ID NO:4. In some embodiments, the amino acid sequence has the sequence shown in SEQ ID NO:4.

In one aspect, a method of making a polypeptide is provided. Such a method typically includes culturing a host cell as described herein under appropriate conditions.

In one aspect, a method for reducing the number of viable *Virgibacillus* in tobacco is provided. Such a method typically includes contacting tobacco with an effective amount of a composition that includes any of the isolated bacteriophage described herein, the isolated nucleic acids described herein, the vectors described herein, the host cells described herein, or the purified polypeptides described herein. In some embodiments, the tobacco is contacted with the composition comprising the bacteriophage prior to fermentation of the tobacco. In some embodiments, the method reduces the level of TSNAs in the tobacco.

In one aspect, an isolated bacteriophage having lytic activity against *Corynebacterium* is provided.

In yet another aspect, a method for reducing the number of viable *Corynebacterium* in tobacco is provided. Such a method typically includes contacting tobacco with an effective amount of a composition that includes any of the isolated bacteriophage described herein, any of the isolated nucleic acids described herein, any of the vectors described herein, any of the host cells described herein, or any of the purified polypeptides described herein. In some embodiments, the tobacco is contacted with the composition including the bacteriophage prior to fermentation of the tobacco. In some embodiments, the method reduces the level of TSNAs in the tobacco.

In one aspect, an isolated bacteriophage having lytic activity against *Staphylococcus* is provided. Such a bacteriophage generally includes a nucleic acid sequence encoding an endolysin, wherein the nucleic acid sequence has at least 95% sequence identity to the nucleic acid sequence shown in SEQ ID NO:5. In some embodiments, the nucleic acid sequence has at least 99% sequence identity to the nucleic acid sequence shown in SEQ ID NO:5. In some embodiments, the nucleic acid sequence has the sequence shown in SEQ ID NO:5. In some embodiments, the endolysin encoded by the nucleic acid sequence has the amino acid sequence shown in SEQ ID NO:6.

In another aspect, an isolated bacteriophage having lytic activity against *Staphylococcus* is provided. Such a bacteriophage generally includes a nucleic acid sequence encoding an endolysin having at least 95% sequence identity to the amino acid sequence shown in SEQ ID NO:6. In some embodiments, the endolysin has at least 99% sequence identity to the amino acid sequence shown in SEQ ID NO:6. In some embodiments, the endolysin has the amino acid sequence shown in SEQ ID NO:6.

In one aspect, an isolated nucleic acid molecule is provided. Such a nucleic acid molecule typically includes a nucleic acid sequence having at least 95% sequence identity to the nucleic acid sequence shown in SEQ ID NO:5. In some embodiments, the nucleic acid molecule comprises a nucleic acid sequence having at least 99% sequence identity to the nucleic acid sequence shown in SEQ ID NO:5. In some embodiments, the nucleic acid molecule comprises a nucleic acid sequence having the sequence shown in SEQ ID NO:5. In some embodiments, the nucleic acid molecule encodes a polypeptide having the amino acid sequence shown in SEQ ID NO:6.

In still another aspect, a vector comprising any of the isolated nucleic acids described herein is provided. In yet another aspect, a host cell comprising a vector as described herein is provided.

In another aspect, a purified polypeptide is provided. Such a polypeptide generally includes an amino acid sequence having at least 95% sequence identity to the amino acid sequence shown in SEQ ID NO:6. In some embodiments, the amino acid sequence has at least 99% sequence identity to the amino acid sequence shown in SEQ ID NO:6. In some embodiments, the amino acid sequence has the sequence shown in SEQ ID NO:6.

In one aspect, a method of making a polypeptide is provided. Such a method generally includes culturing a host cell as described herein under appropriate conditions. In another aspect, a method for reducing the number of viable *Staphylococcus* in tobacco is provided. Such a method typically includes contacting tobacco with an effective amount of a composition comprising an isolated bacteriophage as described herein, an isolated nucleic acid as described herein, a vector as described herein, a host cell as described herein, or a purified polypeptide as described herein. In some embodiments, the tobacco is contacted with the composition comprising the bacteriophage prior to fermentation of the tobacco. In some embodiments, the method reduces the level of TSNAs in the tobacco.

In one aspect, an isolated bacteriophage having lytic activity against *Staphylococcus* is provided. Such a bacteriophage generally includes a nucleic acid sequence encoding an endolysin, wherein the nucleic acid sequence has at least 95% sequence identity to the nucleic acid sequence shown in SEQ ID NO:7. In some embodiments, the nucleic acid sequence has at least 99% sequence identity to the nucleic acid sequence shown in SEQ ID NO:7. In some embodiments, the nucleic acid sequence has the sequence shown in SEQ ID NO:7. In some embodiments, the endolysin encoded by the nucleic acid sequence has the amino acid sequence shown in SEQ ID NO:8.

In another aspect, an isolated bacteriophage having lytic activity against *Staphylococcus* is provided. Such a bacteriophage generally includes a nucleic acid sequence encoding an endolysin having at least 95% sequence identity to the amino acid sequence shown in SEQ ID NO:8. In some embodiments, the endolysin has at least 99% sequence identity to the amino acid sequence shown in SEQ ID NO:8. In some embodiments, the endolysin has the amino acid sequence shown in SEQ ID NO:8.

In one aspect, an isolated nucleic acid molecule is provided. Such a nucleic acid molecule typically includes a nucleic acid sequence having at least 95% sequence identity to the nucleic acid sequence shown in SEQ ID NO:7. In some embodiments, the nucleic acid molecule comprises a nucleic acid sequence having at least 99% sequence identity to the nucleic acid sequence shown in SEQ ID NO:7. In some embodiments, the nucleic acid molecule comprises a nucleic acid sequence having the sequence shown in SEQ ID NO:7. In some embodiments, the nucleic acid molecule encodes a polypeptide having the amino acid sequence shown in SEQ ID NO:8.

In still another aspect, a vector comprising any of the isolated nucleic acids described herein is provided. In yet another aspect, a host cell comprising a vector as described herein is provided.

In another aspect, a purified polypeptide is provided. Such a polypeptide generally includes an amino acid sequence having at least 95% sequence identity to the amino acid sequence shown in SEQ ID NO:8. In some embodiments, the amino acid sequence has at least 99% sequence identity to the amino acid sequence shown in SEQ ID NO:8. In some embodiments, the amino acid sequence has the sequence shown in SEQ ID NO:8.

In one aspect, a method of making a polypeptide is provided. Such a method generally includes culturing a host cell as described herein under appropriate conditions. In another aspect, a method for reducing the number of viable *Staphylococcus* in tobacco is provided. Such a method typically includes contacting tobacco with an effective amount of a composition comprising an isolated bacteriophage as described herein, an isolated nucleic acid as described herein, a vector as described herein, a host cell as described herein, or a purified polypeptide as described herein. In some embodiments, the tobacco is contacted with the composition comprising the bacteriophage prior to fermentation of the tobacco. In some embodiments, the method reduces the level of TSNAs in the tobacco.

In one aspect, an isolated bacteriophage having lytic activity against Carnobacteriaceae is provided. Such a bacteriophage generally includes a nucleic acid sequence encoding an endolysin, wherein the nucleic acid sequence has at least 95% sequence identity to the nucleic acid sequence shown in SEQ ID NO:9. In some embodiments, the nucleic acid sequence has at least 99% sequence identity to the nucleic acid sequence shown in SEQ ID NO:9. In some embodiments, the nucleic acid sequence has the sequence shown in SEQ ID NO:9. In some embodiments, the endolysin encoded by the nucleic acid sequence has the amino acid sequence shown in SEQ ID NO:10.

In another aspect, an isolated bacteriophage having lytic activity against Carnobacteriaceae is provided. Such a bacteriophage generally includes a nucleic acid sequence encoding an endolysin having at least 95% sequence identity to the amino acid sequence shown in SEQ ID NO:10. In some embodiments, the endolysin has at least 99% sequence identity to the amino acid sequence shown in SEQ ID NO:10. In some embodiments, the endolysin has the amino acid sequence shown in SEQ ID NO:10.

In one aspect, an isolated nucleic acid molecule is provided. Such a nucleic acid molecule typically includes a nucleic acid sequence having at least 95% sequence identity to the nucleic acid sequence shown in SEQ ID NO:9. In some embodiments, the nucleic acid molecule comprises a nucleic acid sequence having at least 99% sequence identity to the nucleic acid sequence shown in SEQ ID NO:9. In some embodiments, the nucleic acid molecule comprises a nucleic acid sequence having the sequence shown in SEQ ID NO:9. In some embodiments, the nucleic acid molecule encodes a polypeptide having the amino acid sequence shown in SEQ ID NO:10.

In still another aspect, a vector comprising any of the isolated nucleic acids described herein is provided. In yet another aspect, a host cell comprising a vector as described herein is provided.

In another aspect, a purified polypeptide is provided. Such a polypeptide generally includes an amino acid sequence having at least 95% sequence identity to the amino acid sequence shown in SEQ ID NO:10. In some embodiments, the amino acid sequence has at least 99% sequence identity to the amino acid sequence shown in SEQ ID NO:10. In some embodiments, the amino acid sequence has the sequence shown in SEQ ID NO:10.

In one aspect, a method of making a polypeptide is provided. Such a method generally includes culturing a host cell as described herein under appropriate conditions. In another aspect, a method for reducing the number of viable Carnobacteriaceae in tobacco is provided. Such a method typically includes contacting tobacco with an effective amount of a composition comprising an isolated bacteriophage as described herein, an isolated nucleic acid as described herein, a vector as described herein, a host cell as described herein, or a purified polypeptide as described herein. In some embodiments, the tobacco is contacted with the composition comprising the bacteriophage prior to fermentation of the tobacco. In some embodiments, the method reduces the level of TSNAs in the tobacco.

In one aspect, an isolated bacteriophage having lytic activity against *Virgibacillus* is provided. Such a bacteriophage generally includes a nucleic acid sequence encoding an endolysin, wherein the nucleic acid sequence has at least 95% sequence identity to the nucleic acid sequence shown in SEQ ID NO:11. In some embodiments, the nucleic acid sequence has at least 99% sequence identity to the nucleic acid sequence shown in SEQ ID NO:11. In some embodiments, the nucleic acid sequence has the sequence shown in SEQ ID NO:11. In some embodiments, the endolysin encoded by the nucleic acid sequence has the amino acid sequence shown in SEQ ID NO:12.

In another aspect, an isolated bacteriophage having lytic activity against *Virgibacillus* is provided. Such a bacteriophage generally includes a nucleic acid sequence encoding an endolysin having at least 95% sequence identity to the amino acid sequence shown in SEQ ID NO:12. In some embodiments, the endolysin has at least 99% sequence identity to the amino acid sequence shown in SEQ ID NO:12. In some embodiments, the endolysin has the amino acid sequence shown in SEQ ID NO:12.

In one aspect, an isolated nucleic acid molecule is provided. Such a nucleic acid molecule typically includes a nucleic acid sequence having at least 95% sequence identity to the nucleic acid sequence shown in SEQ ID NO:11. In some embodiments, the nucleic acid molecule comprises a nucleic acid sequence having at least 99% sequence identity to the nucleic acid sequence shown in SEQ ID NO:11. In some embodiments, the nucleic acid molecule comprises a nucleic acid sequence having the sequence shown in SEQ ID NO:11. In some embodiments, the nucleic acid molecule encodes a polypeptide having the amino acid sequence shown in SEQ ID NO:12.

In still another aspect, a vector comprising any of the isolated nucleic acids described herein is provided. In yet another aspect, a host cell comprising a vector as described herein is provided.

In another aspect, a purified polypeptide is provided. Such a polypeptide generally includes an amino acid sequence having at least 95% sequence identity to the amino acid sequence shown in SEQ ID NO:12. In some embodiments, the amino acid sequence has at least 99% sequence identity to the amino acid sequence shown in SEQ ID NO:12. In some embodiments, the amino acid sequence has the sequence shown in SEQ ID NO:12.

In one aspect, a method of making a polypeptide is provided. Such a method generally includes culturing a host cell as described herein under appropriate conditions. In another aspect, a method for reducing the number of viable *Virgibacillus* in tobacco is provided. Such a method typically includes contacting tobacco with an effective amount of a composition comprising an isolated bacteriophage as described herein, an isolated nucleic acid as described herein, a vector as described herein, a host cell as described herein, or a purified polypeptide as described herein. In some embodiments, the tobacco is contacted with the composition comprising the bacteriophage prior to fermentation of the tobacco. In some embodiments, the method reduces the level of TSNAs in the tobacco.

In another aspect, tobacco comprising one or more bacteriophages against a bacteria selected from the group consisting of Carnobacteriaceae, *Virgibacillus*, *Staphylococcus* and *Corynebacterium* is provided. In some embodiments, such a tobacco is aged and cured. In some embodiments, the bacteriophage is selected from any of the bacteriophage described herein.

In one aspect, a tobacco product is provided that includes such tobacco. Representative tobacco product include, without limitation, smokeless tobacco products, tobacco-derived nicotine products, cigarillos, non-ventilated recess filter cigarettes, vented recess filter cigarettes, cigars, snuff, pipe tobacco, cigar tobacco, cigarette tobacco, chewing tobacco, leaf tobacco, shredded tobacco, and cut tobacco.

Unless otherwise defined, all technical and scientific terms used herein have the same meaning as commonly understood by one of ordinary skill in the art to which the methods and compositions of matter belong. Although methods and materials similar or equivalent to those described herein can be used in the practice or testing of the methods and compositions of matter, suitable methods and materials are described below. In addition, the materials, methods, and examples are illustrative only and not intended to be limiting. All publications, patent applications, patents, and other references mentioned herein are incorporated by reference in their entirety.

DETAILED DESCRIPTION

Figure 1:
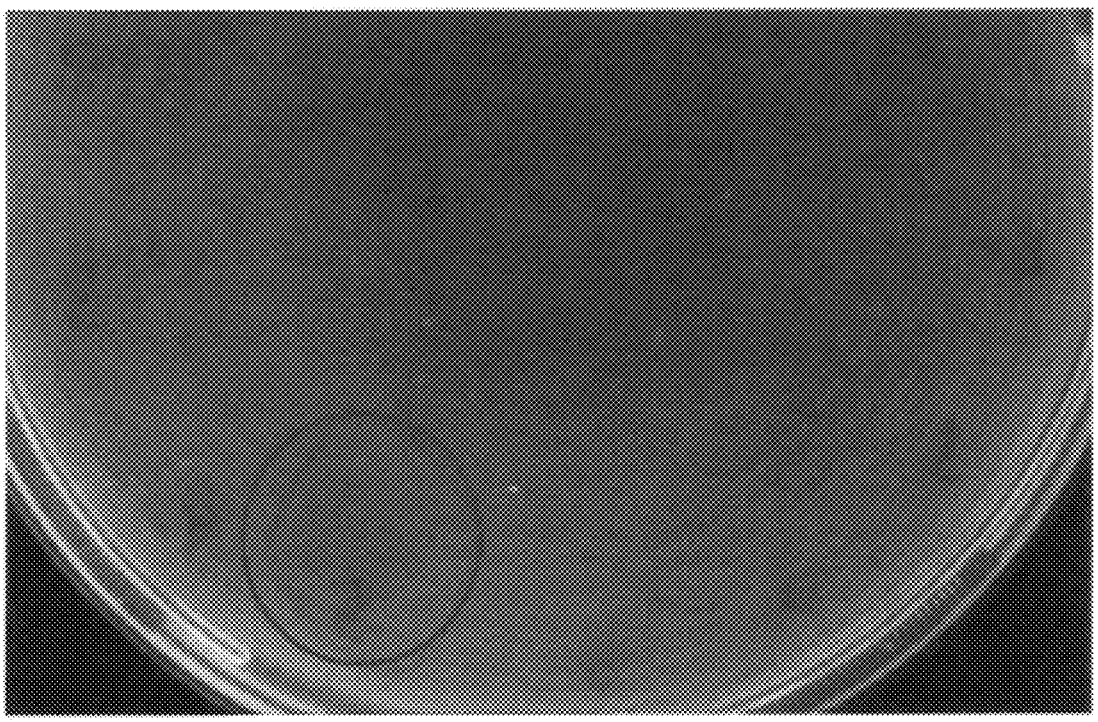
FIG. 1 is a photograph showing the plaques resulting from infection of Carnobacteriaceae with the bacteriophage described herein.

A number of bacteria are present on tobacco growing in a field and at various stages of processing. Some of those bacteria are beneficial and, for example, contribute to the flavor profiles of tobacco, while some of those bacteria are undesirable and, for example, damage the tobacco and contribute to the production of unwanted tobacco-specific nitrosamines (TSNAs).

Bacteriophage Compositions

A number of isolated bacteriophage are provided herein, as well as progeny thereof. As used herein with respect to bacteriophage, "isolated" refers to a bacteriophage that has been separated from the environment in which it is naturally found (e.g., that does not contain a significant amount of other bacteriophage or of the bacterial host). As used herein, "progeny" refers to replicates of a bacteriophage, including descendants of a bacteriophage created by serial passage or other methods known in the art.

In addition to bacteriophage, a bacteriophage composition also can include media, buffers, one or more nutrients, one or more minerals, one or more co-factors, or any other component that is necessary to maintain viability of the bacteriophage. Additionally, components that are not related to the viability of the bacteriophage may be desirable in a bacteriophage composition such as, without limitation, a dye or color marker.

Bacteriophage Nucleic Acids and Polypeptides

Bacteriophage contain endolysins, a generic term for one or more enzymes that are involved in the degradation of the peptidoglycan in the bacterial cell wall, ultimately resulting in lysis of the bacteria. The specificity exhibited by the bacteriophage for a particular bacteria strain is typically attributed to the endolysin(s). Therefore, as described herein, isolated bacteriophage nucleic acids are provided that encode for the endolysins, and the purified endolysin polypeptides also are provided.

The endolysin gene from the bacteriophage against Carnobacteriaceae has the nucleic acid sequence shown in SEQ ID NO:1 and encodes an endolysin polypeptide having the sequence shown in SEQ ID NO:2; the endolysin gene from the bacteriophage against *Virgibacillus* has the nucleic acid sequence shown in SEQ ID NO:3 and encodes a polypeptide having the sequence shown in SEQ ID NO:4; the endolysin gene from the bacteriophage against *Staphylococcus* has the nucleic acid sequence shown in SEQ ID NO:5 and encodes an endolysin polypeptide having the sequence shown in SEQ ID NO:6; the endolysin gene from the bacteriophage against *Staphylococcus* has the nucleic acid sequence shown in SEQ ID NO:7 and encodes a polypeptide having the sequence shown in SEQ ID NO:8; the endolysin gene from the bacteriophage against Carnobacteriaceae has the nucleic acid sequence shown in SEQ ID NO:9 and encodes an endolysin polypeptide having the sequence shown in SEQ ID NO:10; and the endolysin gene from the bacteriophage against *Virgibacillus* has the nucleic acid sequence shown in SEQ ID NO:11 and encodes a polypeptide having the sequence shown in SEQ ID NO:12.

In addition to the nucleic acid sequences shown in SEQ ID NOs:1, 3, 5, 7, 9 and 11, and the polypeptide sequences shown in SEQ ID NOs: 2, 4, 6, 8, 10 and 12, nucleic acid and polypeptide sequences are provided that differ in sequence from SEQ ID NOs: 1, 3, 5, 7, 9 and 11, and SEQ ID NOs: 2, 4, 6, 8, 10 and 12, respectively. For example, nucleic acid sequences having at least 70% sequence identity (e.g., at least 75%, 80%, 85%, 90%, 95%, 99% or 100% sequence identity) to any of the nucleic acid sequences shown in SEQ ID NOs: 1, 3, 5, 7, 9 and 11 are provided. Similarly, amino acid sequences having at least 70% sequence identity (e.g., at least 75%, 80%, 85%, 90%, 95%, 99% or 100% sequence identity) to any of the amino acid sequences shown in SEQ ID NOs: 2, 4, 6, 8, 10 and 12 are provided.

To calculate the percent sequence identity of two sequences, the first and second sequences are aligned and the number of identical matches of nucleotides or amino acid residues between the two sequences is determined. The number of identical matches is divided by the length of the aligned region (i.e., the number of aligned nucleotides or amino acid residues) and multiplied by 100 to arrive at a percent sequence identity value. It will be appreciated that the length of the aligned region can be a portion of one or both sequences up to the full-length size of the shortest sequence. It also will be appreciated that a single sequence can align differently with other sequences and hence, can have different percent sequence identity values over each aligned region. Two sequences can be aligned to determine percent sequence identity using the algorithm described by Altschul et al. (1997, *Nucleic Acids Res.*, 25:3389-3402), which is incorporated into BLAST (basic local alignment search tool) programs available at ncbi.nlm.nih.gov on the World Wide Web.

With respect to nucleic acids, an "isolated" nucleic acid refers to a nucleic acid that is separated from other nucleic acids that are usually associated with the isolated nucleic acid. Thus, an "isolated" nucleic acid includes, without limitation, a nucleic acid that is free of sequences that naturally flank one or both ends of the nucleic acid in the genome of the organism from which the isolated nucleic acid is derived (e.g., a cDNA or genomic DNA fragment produced by PCR or restriction endonuclease digestion). In addition, an isolated nucleic acid molecule can include an engineered nucleic acid molecule such as a recombinant or a synthetic nucleic acid molecule. With respect to polypeptides, a "purified" polypeptide refers to a polypeptide that has been separated or purified from cellular components that naturally accompany it. Typically, the polypeptide is considered "purified" when it is at least 70% (e.g., at least 75%, 80%, 85%, 90%, 95%, or 99%) by dry weight, free from the proteins and naturally occurring molecules with which it is naturally associated. Since a polypeptide that is chemically synthesized is, by nature, separated from the components that naturally accompany it, a synthetic polypeptide is "purified."

The nucleic acids described herein (e.g., encoding the bacteriophage endolysin polypeptides) can be introduced into vectors. Vectors, including expression vectors, are commercially available or can be produced by routine molecular biology methods. A vector containing a bacteriophage nucleic acid also can have elements necessary for expression operably linked to the bacteriophage nucleic acid, and a vector further can include sequences such as those encoding a selectable marker (e.g., an antibiotic resistance gene) and/or sequences that can be used in purification of a polypeptide (e.g., 6×His tag).

Elements necessary for expression include nucleic acid sequences that direct and regulate expression of nucleic acid coding sequences such as, for example, promoter sequences. Elements necessary for expression also can include introns, enhancer sequences, response elements, or inducible elements that modulate expression of a nucleic acid. As used herein, operably linked means that an element necessary for expression (e.g., a promoter and/or other regulatory element) is positioned in a vector relative to a nucleic acid coding sequence in such a way as to direct or regulate expression of the nucleic acid coding sequence.

Vectors containing a bacteriophage nucleic acid can be introduced into host cells. Methods of introducing nucleic acids into host cells are known in the art and include, without limitation, calcium phosphate precipitation, electroporation, heat shock, lipofection, microinjection, and viral-mediated nucleic acid transfer. The term "host cell" refers not only to the particular cell but also to the progeny or potential progeny of such a cell. A host cell can be any prokaryotic or eukaryotic cell. For example, nucleic acids can be expressed in bacterial cells such as, without limitation, *E. coli*, or in insect cells, yeast cells, or mammalian cells such as Chinese hamster ovary (CHO) cells or COS cells. It would be appreciated by those skilled in the art that the natural infection process of bacteriophage can be used to introduce a nucleic acid or nucleic acid vector into a bacterial cell.

Methods of Using Bacteriophage Compositions and Bacteriophage Nucleic Acids and Polypeptides Any of the bacteriophages described herein (i.e., bacteriophage against Carnobacteriaceae sp., *Virgibacillus* sp., *Staphylococcus* sp. and *Corynebacterium* sp.), or the endolysin nucleic acids or polypeptides from any of the bacteriophage described herein, can be used in methods of reducing the number and/or growth of Carnobacteriaceae sp., *Virgibacillus* sp., *Staphylococcus* sp. or *Corynebacterium* sp. bacteria. For example, tobacco (e.g., blends of tobacco used to manufacture smokeless tobacco products) can be contacted with an effective amount of any of the bacteriophages described herein, or any of the bacteriophage endolysin nucleic acids or polypeptides described herein. The tobacco can be contacted with an effective amount of one or more of the indicated bacteriophage, or an endolysin nucleic acid or polypeptide, prior to, during and/or after fermentation of the tobacco, and/or at the finishing stage.

Briefly, after harvesting, tobacco can be cured using conventional means, e.g., air curing, fire curing, barn curing, sun curing. See, for example, Tso (1999, Chapter I in Tobacco, Production, Chemistry and Technology, Davis & Nielsen, Eds., Blackwell Publishing, Oxford). Optionally, cured tobacco then can be conditioned and/or fermented. Conditioning includes, for example, a heating, sweating or pasteurization step as described in U.S. Publication Nos. 2004/0118422 or 2005/0178398. Fermenting typically is characterized by high initial moisture content, heat generation, and a 10 to 20% loss of dry weight. See, for example, U.S. Pat. Nos. 4,528,993; 4,660,577; 4,848,373; and 5,372,149. Cured or cured and fermented tobacco then can be further processed (e.g., cut, expanded, blended, milled or comminuted).

Contacting tobacco during the processing and finishing of the products with any of the bacteriophage or bacteriophage endolysins described herein (e.g., bacteriophage against *Carnobacteriaceae*, *Virgibacillus*, or *Corynebacterium*) results in a number of benefits or improvements to the tobacco including, without limitation, a reduction in the level of TSNAs in the tobacco, and an increased shelf-life of the tobacco product. A reduction in the level of TSNAs is defined as a reduction in at least 10% (e.g., at least 15%, 20%, 25%, 30%, 40%, 50% or more) TSNAs in bacteriophage-contacted tobacco relative to tobacco not contacted with bacteriophage. The shelf life of a tobacco product is increased if the tobacco in the tobacco product maintains its sensory characteristics (e.g., mouth feel, flavor profile, etc.)

for a longer period of time than a comparable tobacco product containing tobacco cured and processed under comparable conditions but without bacteriophage (a "control" tobacco product). Under certain circumstances, the shelf life of the tobacco product containing the bacteriophage-contacted tobacco is statistically significantly longer than the shelf life of a control tobacco product. As used herein, "statistically significantly" refers to a p-value of less than 0.05 (e.g., less than 0.025 or 0.01) using an appropriate measure of statistical significance (e.g., a one-tailed two-sample t-test).

As used herein, a reduction in the number of viable bacteria means a reduction in the number of bacteria that are alive and capable of, for example, replication. For example, lysed bacteria or bacteria in the process of lysing are not considered viable. The viability of bacteria can be determined using methods routinely used in microbiology. These reductions (i.e., in the number of viable bacteria) in the presence of any of the bacteriophage (or endolysin nucleic acid or polypeptide) described herein are a result of the lytic activity exerted by the bacteriophage (or endolysin nucleic acid or polypeptide) on the bacteria. As used herein, an "effective amount" of a bacteriophage or of an endolysin nucleic acid or polypeptide is an amount that results in lysis of bacteria in an amount or at a rate that is sufficient to reduce the number of viable bacteria to a desired level.

Methods of Obtaining Bacteriophage Compositions

Methods of obtaining bacteriophage are known in the art. See, for example, *Bacteriophages: Methods and Protocols*, Volume 1: Isolation, Characterization, and Interactions (Methods in Molecular Biology), Eds, Clokie & Kropinski, 2010, Humana Press; Seeley et al., 1982, J. Applied Bacteriol., 53:1-17; Pope et al., 2011, PLoS ONE, 6:e16329; and Hendrix et al., 1999, PNAS USA, 96:2192-7. Briefly, bacteria of interest (e.g., the target bacteria) are obtained, generally using standard culture methods. Typically, bacteria are cultured in such as way so as to activate the lytic phase of bacteriophage native to the bacteria and cause lysis. Following lysis of the bacteria, the bacteriophage is collected and can be characterized using any number of known methods such as, without limitation, nucleic acid sequencing, electron microscopy, burst size, and/or attachment rate. Bacteriophage also can be described based on their host (i.e., host profiling).

Tobacco Products

Tobacco products for adult tobacco consumers are provided that contain tobacco (e.g., whole leaf, stems, and cut, chopped or comminuted leaf or stem) that has been contacted with one or more bacteriophage (i.e., bacteriophage against Carnobacteriaceae sp., *Virgibacillus* sp., *Staphylococcus* sp. or *Corynebacterium* sp., or endolysin nucleic acids or polypeptides from any of such bacteriophages).

Under certain circumstances, the tobacco or reconstituted leaf can undergo one or more treatments in order to remove or inactivate the bacteriophage once the amount and/or growth of the respective bacteria has reached an acceptable level. However, since bacteriophage are in the generally recognized as safe (GRAS) category, the bacteriophage may be present in the final tobacco product. For example, in certain embodiments, one or more bacteriophage (or one or more endolysin proteins) can be present in a final tobacco product, such as, without limitation, a container of moist smokeless tobacco, in loose form or in a pouch.

Tobacco products are known in the art and include any product made or derived from tobacco that is intended for human consumption, including any component, part, or accessory of a tobacco product. Representative tobacco products include, without limitation, smokeless tobacco products, tobacco-derived nicotine products, cigarillos, non-ventilated recess filter cigarettes, vented recess filter cigarettes, cigars, snuff, pipe tobacco, cigar tobacco, cigarette tobacco, chewing tobacco, leaf tobacco, shredded tobacco, and cut tobacco. Representative smokeless tobacco products include, for example, chewing tobacco, snus, pouches, films, tablets, coated dowels, rods, and the like. Representative cigarettes and other smoking articles include, for example, smoking articles that include filter elements or rod elements, where the rod element of a smokeable material can include cured tobacco within a tobacco blend. In addition to the tobacco described herein (i.e., that includes one or more bacteriophages), tobacco products also can include other ingredients such as, without limitation, binders, plasticizers, stabilizers, and/or flavorings. See, for example, US 2005/0244521, US 2006/0191548, US 2012/0024301, US 2012/0031414, and US 2012/0031416 for examples of tobacco products. Suitable packaging is known for the various types of tobacco products.

In accordance with the present invention, there may be employed conventional molecular biology, microbiology, biochemical, and recombinant DNA techniques within the skill of the art. Such techniques are explained fully in the literature. The invention will be further described in the following examples, which do not limit the scope of the methods and compositions of matter described in the claims.

EXAMPLES

Example 1—Isolation of Bacteriophages from Tobacco

Smokeless tobacco products and tobacco materials were used to isolate bacteriophages. 30 grams of the solid tobacco samples was added to 270 g of the low salt (5%) diluent in a filtered stomacher bag. The sample was mixed using a stomacher for 3 minutes at 200 RPM. The sample was then poured from the filtered side of the stomacher bag into a centrifuge tube and centrifuged for 30 minutes at 11,000×g. The supernatant was poured off and passed sequentially through a 0.45 micron and 0.22 micron filter. The sterile filtrate was subjected to ultracentrifugation. 15 ml of the filtrate was added to the Amicon Ultra-15 Centrifugal Filter Device. The devices were centrifuged for 30 minutes at 1,500×g to concentrate and separate the phages from the filtrate. 15 ml of the filtrate was then concentrated to 250 to 500 µl.

The filtrates were then combined 1:1 with 2× Tryptic Soy Broth (TSB), 2× low salt broth, 2× high salt broth, 2× 15% salt broth (pH 8), 2× 10% salt broth (pH 9 and pH 7.4). Each of the filtrate broth combinations, now referred to as enrichments, were then inoculated with 1 ml of a turbid culture of interest. Carnobacteriaceae, *Virgibacillus, Staphylococcus* and *Corynebacterium* were separately inoculated into each of the enrichments and incubated for 21, 24 and 18 days, respectively. 2 ml of the enrichment was removed after incubation and centrifuged for 1 minute at 13,000 RPM. The supernatant was passed through a sterile 0.22 micron filter and placed into a sterile microcentrifuge tube. 10 µl of the sterile filtrates were then dropped on to the appropriate agars with the corresponding soft agars on top. The soft agars contained 100 µl of the appropriate culture for which it was enriched. The spot plates were left to absorb into the agar and then incubated at 32° C. until clear lysis zones developed. The enrichments were placed back into the incubator and processed 4 to 6 more times as stated above before the enrichment series was stopped.

Upon observation of a clear lysis zone (plaque), the plate was removed from the incubator and the plaque was harvested for isolation. The wide end of a 1000 µl tip was placed over the plaque and gently dug into the soft agar overlay of the plate. The soft agar plug was then placed into 1 ml of SM buffer and refrigerated at 4° C. overnight to allow for diffusion of the bacteriophage. 10 µl of the SM buffer containing the phage was then dropped onto the appropriate soft agar with the appropriate strain in the soft agar. The plate was then incubated at 32° C. to confirm lysis of the bacterial strain.

Using these methods, several bacteriophage were identified that are specific against the Carnobacteriaceae, *Virgibacillus, Staphylococcus* and *Corynebacterium* bacteria.

Example 2—Bacteriophage Plaque Formation

Figure 2:
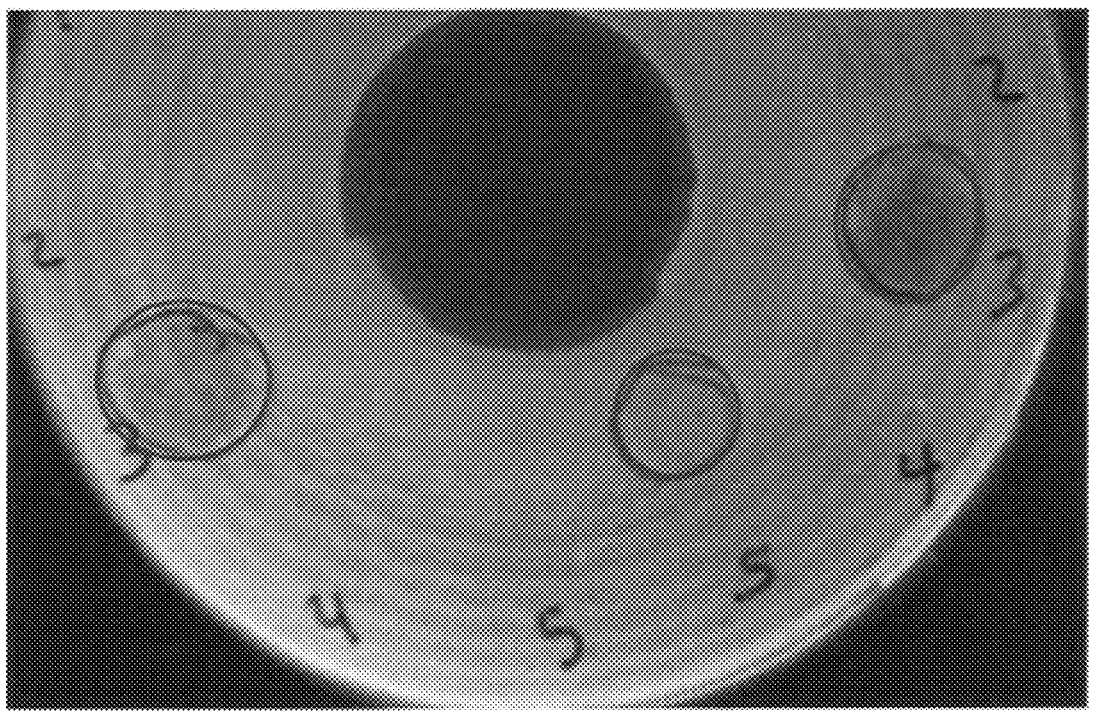
FIG. 2 is a photograph showing the plaques resulting from infection of *Virgibacillus* with the bacteriophage described herein.
Figure 3:
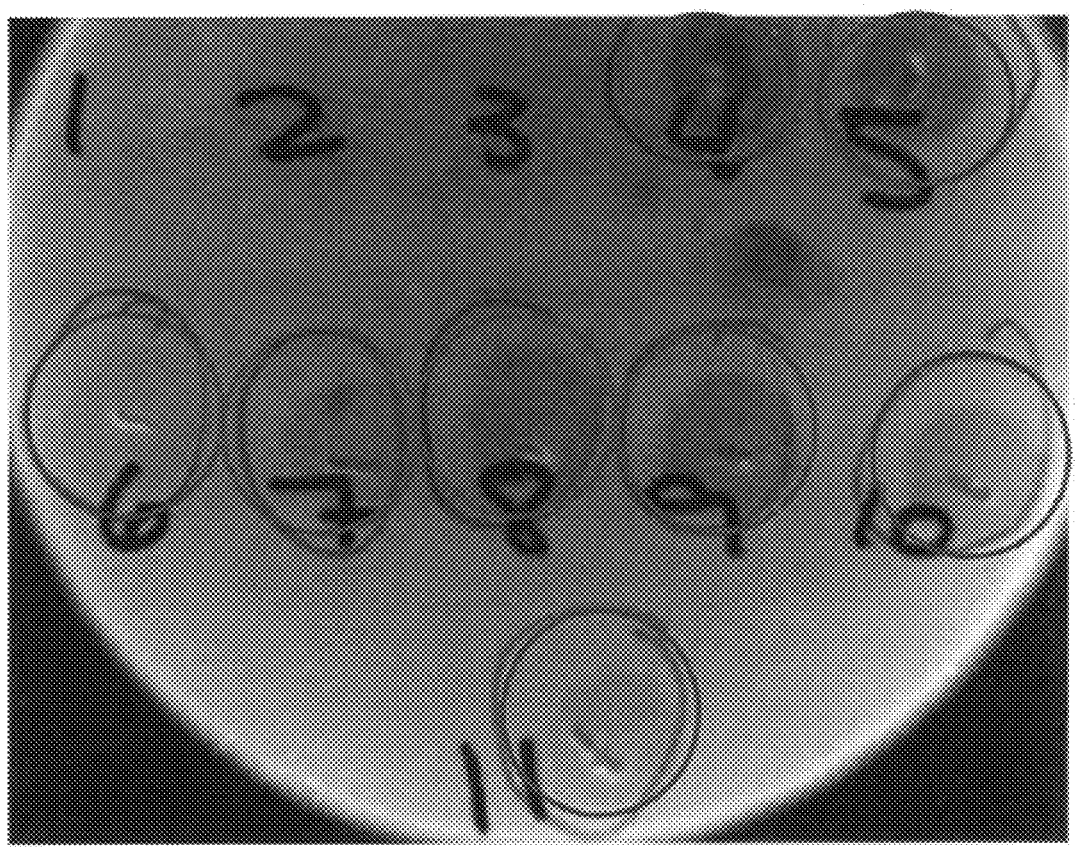
FIG. 3 is a photograph showing the plaques resulting from infection of *Corynebacterium* with the bacteriophage described herein.

FIGS. 1, 2, and 3 show the inhibition of the target bacterial strains in the presence of the phage on soft agar plates. FIG. 1 shows a lawn of Carnobacteriaceae from tobacco ultrafiltrate growing on 10% salt agar. The circled area shows a plaque. FIG. 2 shows a lawn of *Virgibacillus* from tobacco ultrafiltrate and Great Salt Lake sterile filtrate (0.22 micron) growing on 5% salt agar. The circled areas show plaques. FIG. 3 shows a lawn of *Corynebacterium* and Great Salt Lake ultrafiltrate growing on 10% salt agar. The circled areas show plaques. Great Salt Lake water samples originally were used as a source of halophilic bacteria and their corresponding bacteriophage; once isolated, use of water samples continued in the culture.

Example 3—In-Silico Analysis of Bacteriophage Genomes

Phage sequence contigs were screened for potential endolysin sequences. All six reading frames of all sequences were translated into amino acid sequences. The obtained amino acid sequences were searched using PFAM domain homology for the identification of potential lytic domain and cell wall binding domains.

Example 4—Cloning of Candidate Endolysin Sequences

Artificial *E. coli* codon optimized gene sequences for candidate proteins were designed and synthesized. The sequences were cloned into BamHI/SalI sites of pQE30 protein expression plasmids and transformed into *E. coli* XL1BlueMRF hosts. Sequence integrities were confirmed by sequencing.

Several derivative endolysin sequences were constructed for comparison purposes. Inter-domain linker sequences were estimated and protein expression vectors harboring the putative cell wall binding domain (CBD) fused to green fluorescence protein (GFP) were constructed. The GFP-CBD fusions were generated to evaluate binding properties of the endolysins to their target cells. CBD sequences were in-frame ligated into SacI/SalI sites of pHGFP vector (Loessner et al., 2002, Mol. Microbiol., 44:335-49).

Example 5—Protein Over-Expression and Partial Purification

Recombinant protein production was performed in Luria Bertani-broth under IPTG induction at 20° C. for 16 h. Cells were lysed in a cell pressure homogenizer and 6×-His tagged proteins were partially purified from cell lysates by immobilized metal affinity chromatography (IMAC) using Zinc loaded IMAC sepharose (GE Healthcare).

Example 6—Lysis and Binding Assays

Purified recombinant endolysins were diluted with PBS buffer (pH 7.4) to a concentration of 2 µM and mixed in a 1:1 ratio with substrate cells adjusted to an optical density at 600 nm (OD600 nm) with the same buffer. Drop in OD600 nm was subsequently monitored for up to 1 hour.

Binding of GFP_CBD proteins to target cells was done by mixing 20 µg proteins with cells from 1 ml culture with an OD600 nm of about 1. Cells were washed twice with 1 ml PBS pH 7.4. Protein binding was evaluated with epi-fluorescence microscopy and images were taken using a confocal laser scanning microscope.

Example 7—Results

Figure 4:
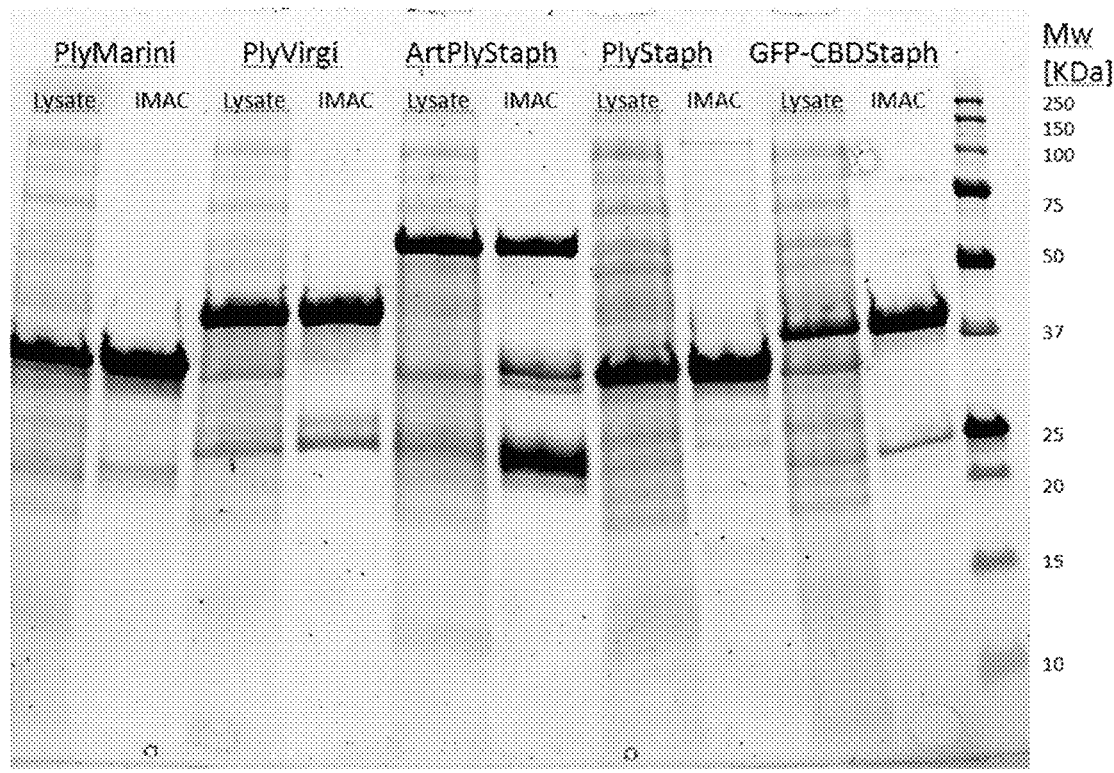
FIG. 4 is a SDS-PAGE gel of cytosolic-expressed proteins in cell lysates and after IMAC purification.

PlyStaph is composed of two domains with the N-terminal domain having homology to Amidase_2 (PFAM01510) domains and the C-terminal domain having homology to SH3_5 (PFAM08460) domains. Usually, endolysins with Staphylococcal background are built of 3 individually folded domains with a Cysteine-Histidine-dependent Amidase/Peptidase domain (CHAP) at the N-terminal end (e.g., CHAP-Amidase-SH3b). In many cases, the CHAP domain contributes most to catalytic activity when applied as exolysins, whereas the amidase domain seems to be virtually inactive. To account for this, a CHAP domain was fused to the N-terminal of PlyStaph and designated "Artificial Phage lysine Staph" or "ArtPlyStaph"). The CHAP domain was identified in a putative structural phage protein found in the same genome. This protein construct was also IMAC purified, but seemed to have some contaminating proteins or degradation products (FIG. 4). Finally, this CHAP domain was also directly fused to the cell wall binding domain of PlyStaph ("TCHAP-CBDStaph").

Figure 5:
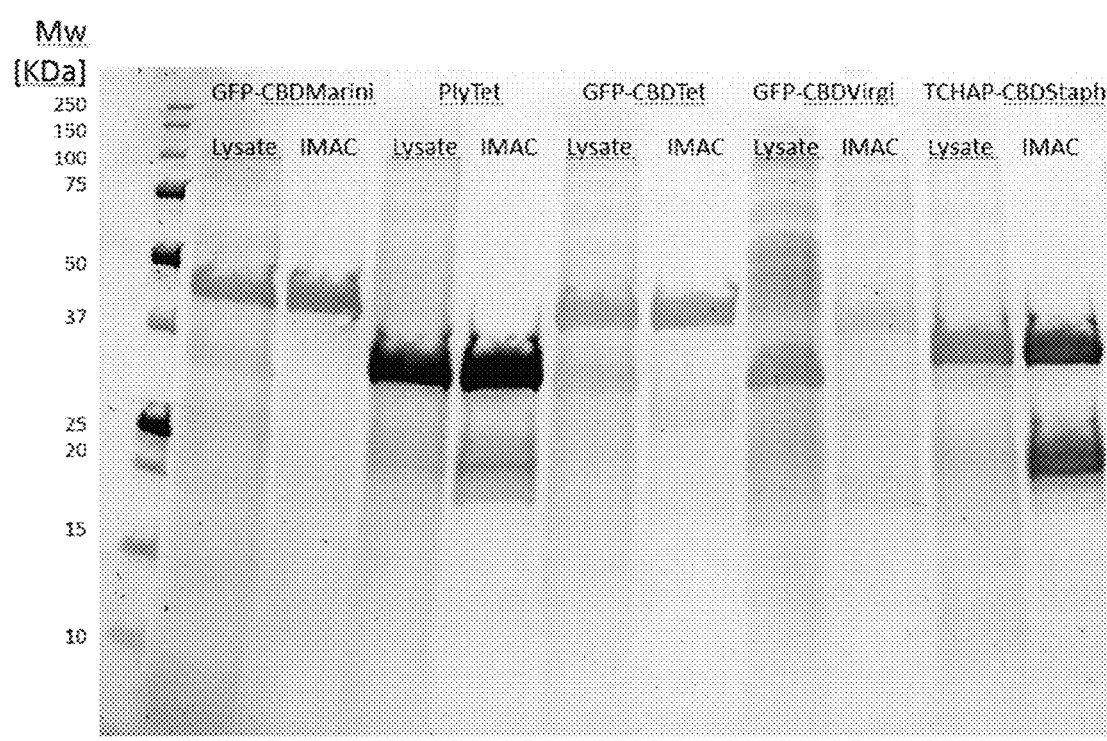
FIG. 5 is a SDS-PAGE gel of cytosolic-expressed proteins in cell lysates and after IMAC purification.
Figure 6:
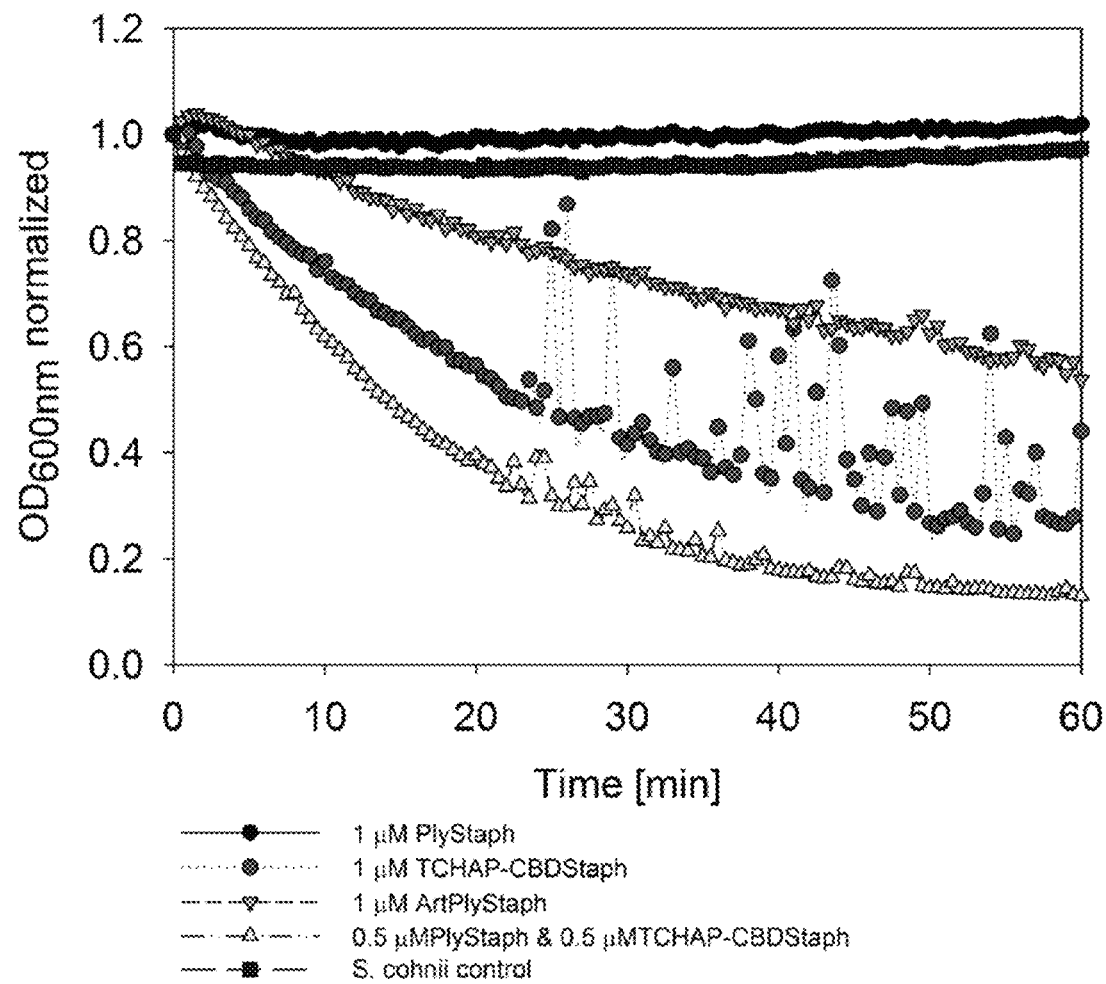
FIG. 6 is a graph showing endolysin activity in a turbidity reduction assay of PlyStaph and derivatives against *S. cohnii*.
Figure 7:
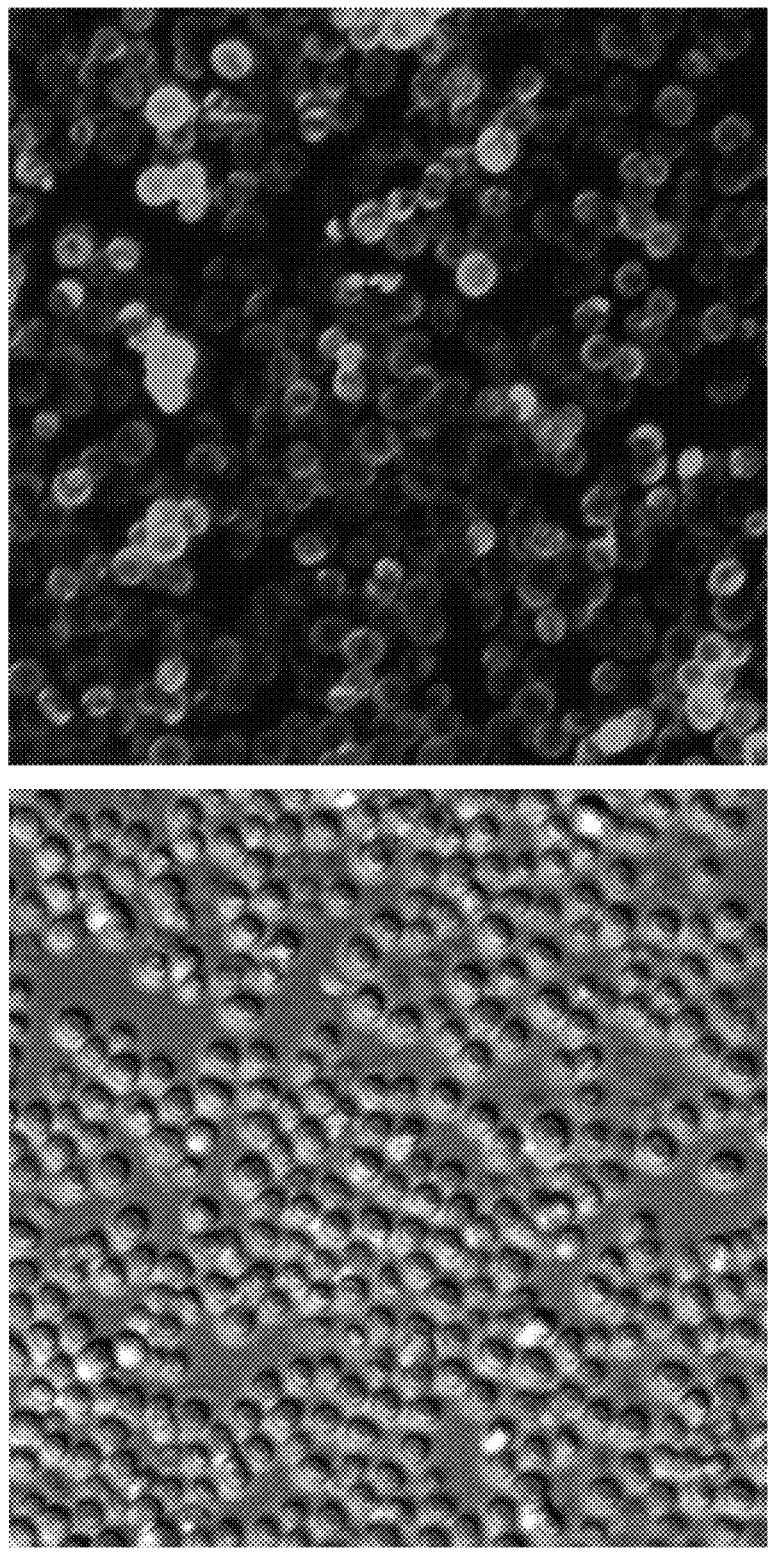
FIG. 7 are photographs showing GFP-CBDStaph binding to *S. cohnii*.
Figure 8:
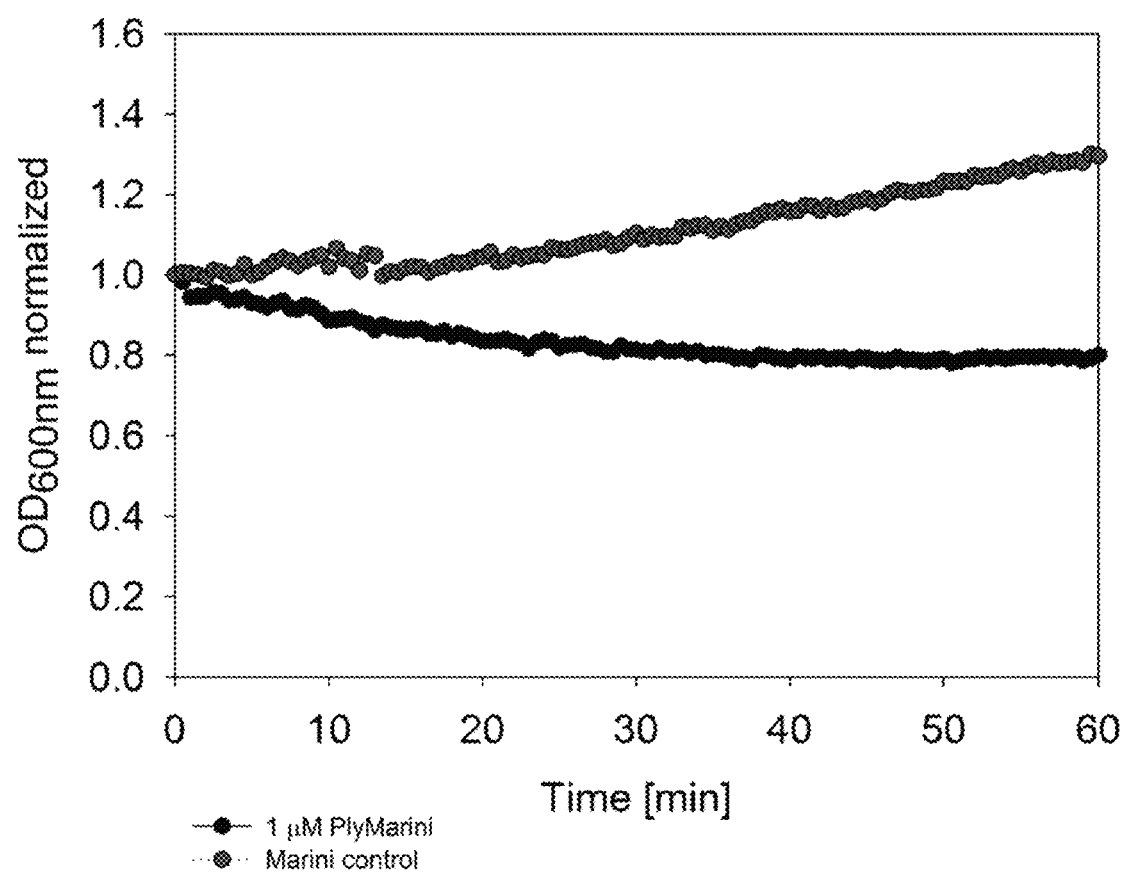
FIG. 8 is a graph showing PlyCarno activity in a turbidity reduction assay. Note that lysis could not be detected. The increase in turbidity in the control is likely to be the result of aggregate formation.
Figure 9:
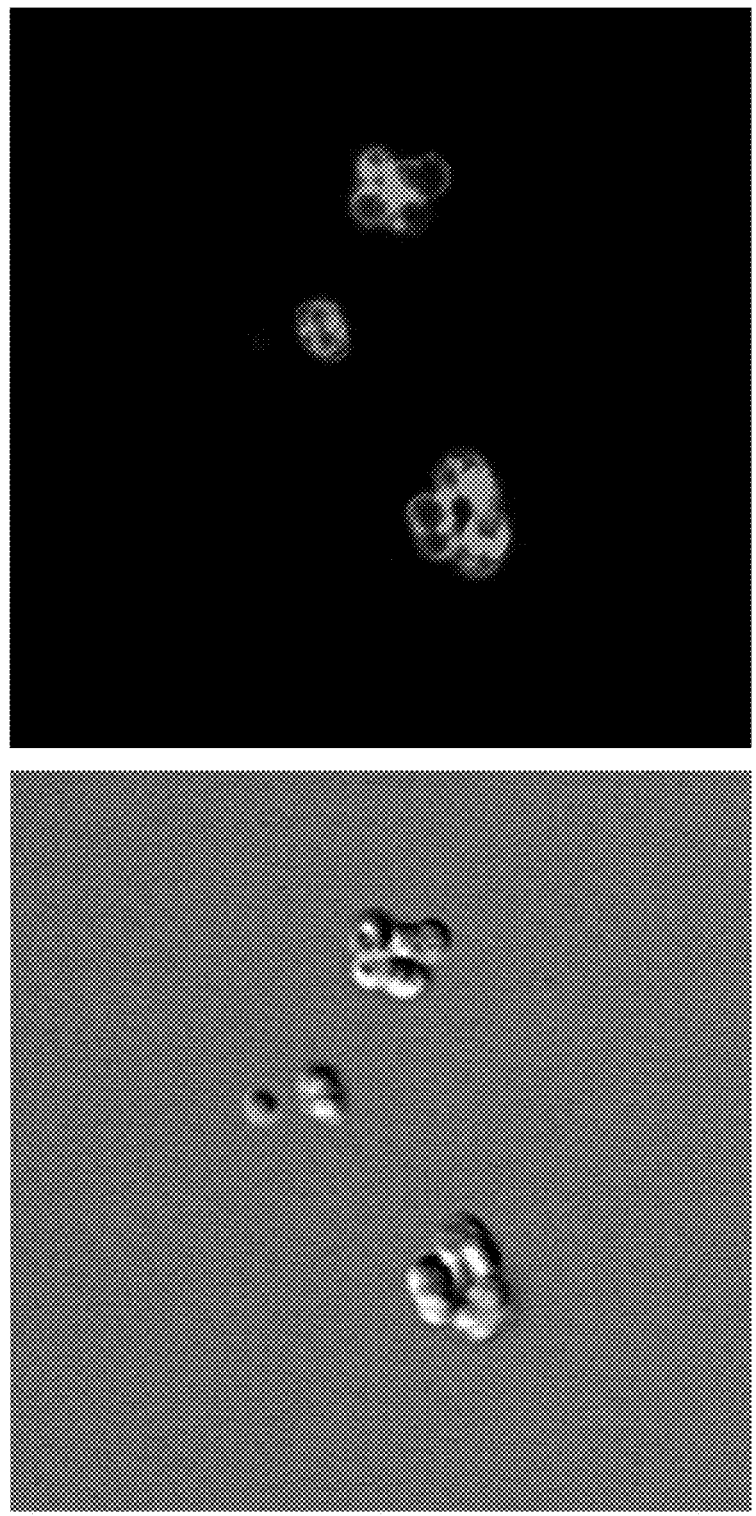
FIG. 9 are photographs showing GFP-CBDCarno binding.
Figure 10:
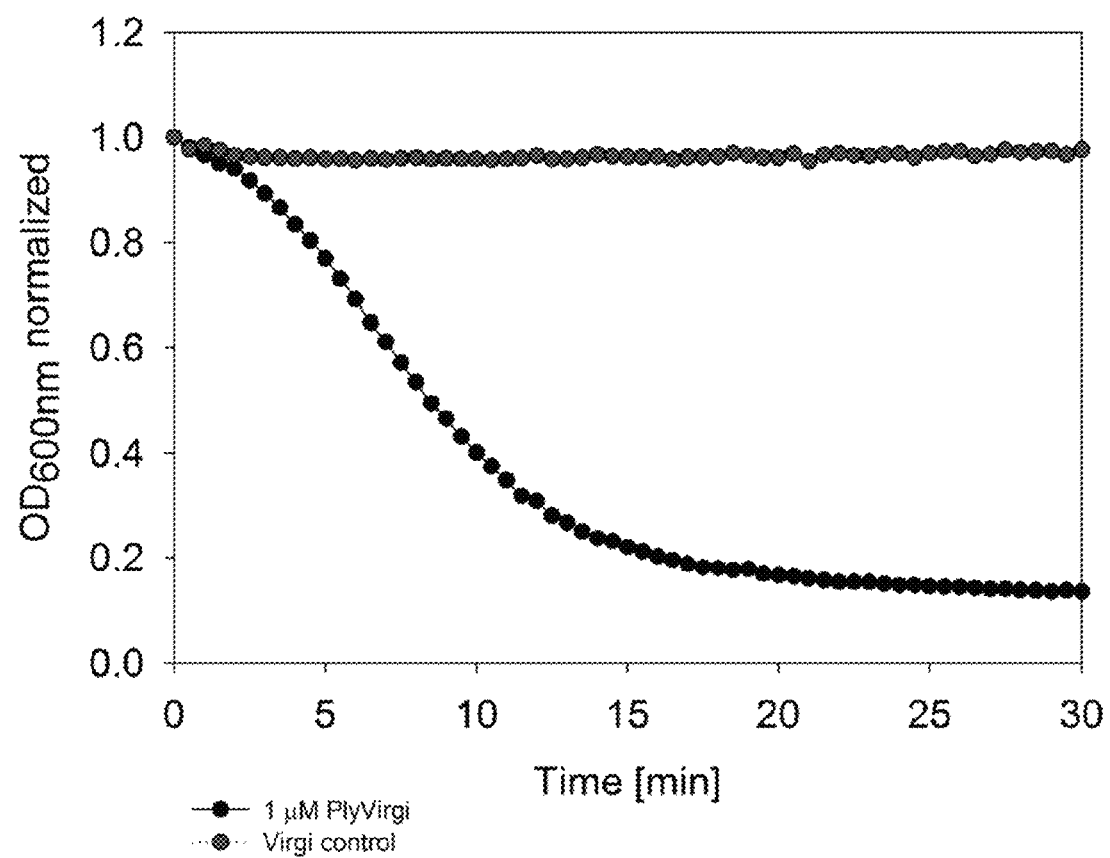
FIG. 10 is a graph showing PlyVirgi activity in a turbidity reduction assay. Please note, that GFP-CBDVirgi protein was not found active. The reason is poor protein quality, rather than a lack of function.
Figure 11:
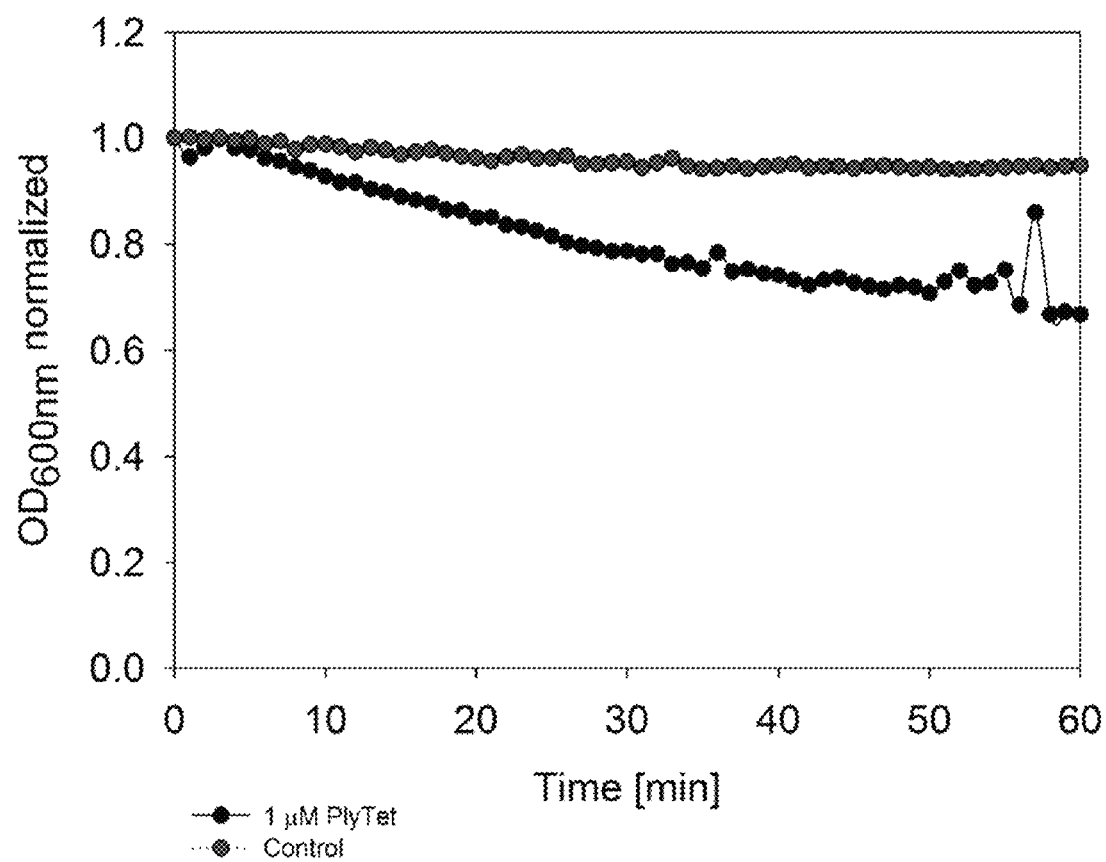
FIG. 11 is a graph showing PlyTet activity in a turbidity reduction assay.
Figure 12:
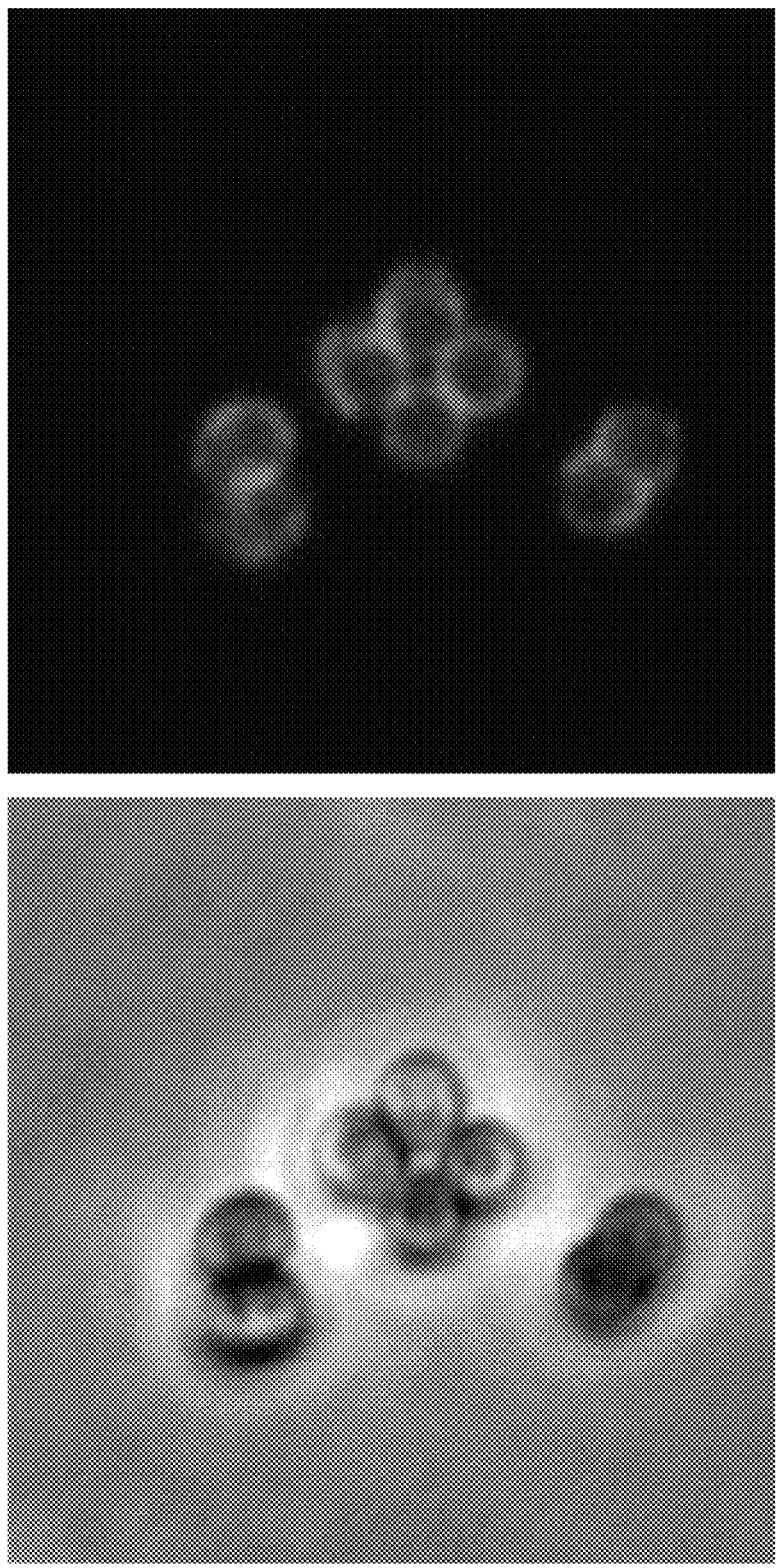
FIG. 12 are photographs showing GFP-CBDTet binding.

All proteins were successfully expressed and partially purified (with the exception of GFP-CBDVirgi, which was not detectable in purified samples). The protein data are provided in Table 1, and FIGS. 4 and 5.

Activity data were collected in a turbidity reduction setup in PBS buffer with 0.1% Tween20 (pH 7.4). Buffer only served as control. Binding of GFP-tagged CBDs to target strains was evaluated under epi-fluorescent light and imaged using a confocal scanning light microscopy setup. The results are presented in FIGS. 6 to 12.

TABLE 1

Protein concentrations after recombinant expression in 700 ml LB-PE medium and IMAC purification

| Protein | Concentration [mg/ml] | Volume [ml] | Total amount [mg] |
| --- | --- | --- | --- |
| PlyMarini | 2.57 | 3 | 7.7 |
| GFP-CBDMarini | 4.51 | 3.2 | 14.43 |
| PlyVirgi | 3.33 | 2.7 | 8.99 |
| GFP-CBDVirgi | 3.16 (poor quality) | 1.2 | 3.8 |
| PlyStaph | 1.23 | 4 | 4.92 |
| ArtPlyStaph | 1.5 | 4 | 6 |
| TCHAP-CBDStaph | 1.97 | 2 | 3.94 |
| GFP-CBDStaph | 4.55 | 2.5 | 11.38 |

TABLE 1-continued

Protein concentrations after recombinant expression
in 700 ml LB-PE medium and IMAC purification

| Protein | Concentration [mg/ml] | Volume [ml] | Total amount [mg] |
|---|---|---|---|
| PlyTet | 7.75 | 2.8 | 21.69 |
| GFP-CBDTet | 1.96 | 3.2 | 6.26 |

Example 8—Endolysin Sequences

Endolysin sequences are provided in SEQ ID NOs: 1-12.
SEQ ID NOs: 1 and 2 are the nucleic acid and polypeptide sequences, respectively, of an endolysin from phage against Carnobacteriaceae bacteria.
SEQ ID NOs: 3 and 4 are the nucleic acid and polypeptide sequences, respectively, of an endolysin from phage against *Virgibacillus* bacteria.
SEQ ID NOs: 5 and 6 are the nucleic acid and polypeptide sequences, respectively, of an endolysin from phage against *Staphylococcus* bacteria.
SEQ ID NOs: 7 and 8 are the nucleic acid and polypeptide sequences, respectively, of an endolysin from phage against *Staphylococcus* bacteria.
SEQ ID NOs: 9 and 10 are the nucleic acid and polypeptide sequences, respectively, of an endolysin from phage against Carnobacteriaceae bacteria.
SEQ ID NOs: 11 and 12 are the nucleic acid and polypeptide sequences, respectively, of an endolysin from phage against *Virgibacillus* bacteria.

Example 9—Endolysin Application in Pure Cultures

Figure 13A:
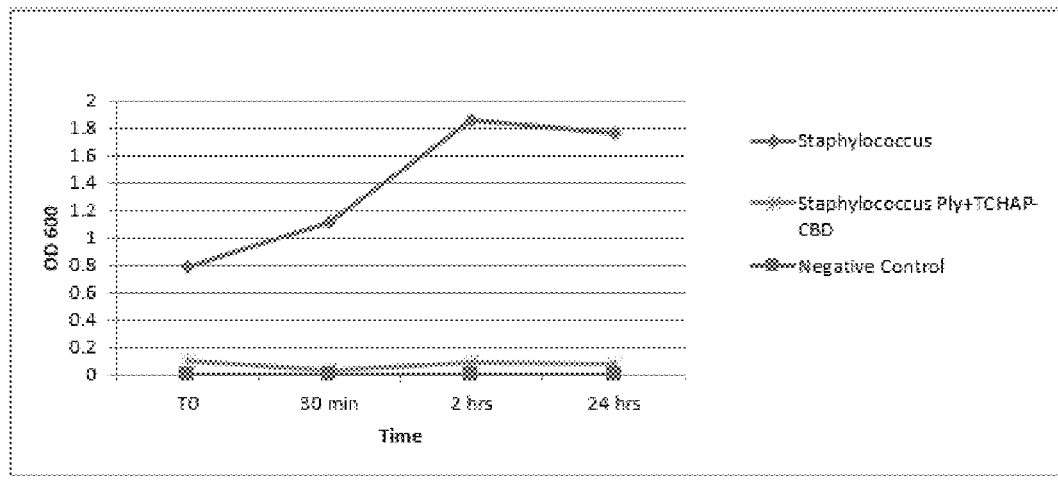
FIG. 13A is a graph showing the effectiveness of a combination of endolysins from two different bacteriophage against *Staphylococcus* in culture.

To determine the effectiveness of the cloned endolysins against Carnobacteriaceae, *Virgibacillus*, and *Staphylococcus*, the bacteria was inoculated into fresh 2× low salt (*Virigibacillus* and *Staphylococcus*) or medium salt broth (Carnobacteriaceae) and incubated at 32° C. for 1-7 days to achieve mid-log growth. The cultures were normalized to an OD600 of 1 using Phosphate Buffered Saline (PBS) with 0.1% Tween 20 at a pH of 7.4. The respective endolysin was added at a concentration of 1 μM and incubated for 24 hours at 32° C. Samples were taken at various time points for OD600 readings and for microbial enumeration. Representative data with *Staphylococcus* and a combination of endolysins from two different bacteriophage against *Staphylococcus* (referred to in Table 1 as "Ply"+"TCHAP-CBD", which correspond to SEQ ID NOs: 6 and 8, respectively) is shown in Table 2 and FIG. 13A.

TABLE 2

| | OD600 | | |
|---|---|---|---|
| Sample Point | Negative Control | *Staphylococcus* | *Staphylococcus* Ply + TCHAP-CBD |
| T0 | 0 | 0.79 | 0.1 |
| 30 min | 0 | 1.12 | 0.03 |
| 2 hrs | 0 | 1.85 | 0.09 |
| 24 hrs | 0 | 1.76 | 0.08 |

Example 10—Bacteriophage or Endolysin Application in Moist Smokeless Tobacco

Figure 13B:
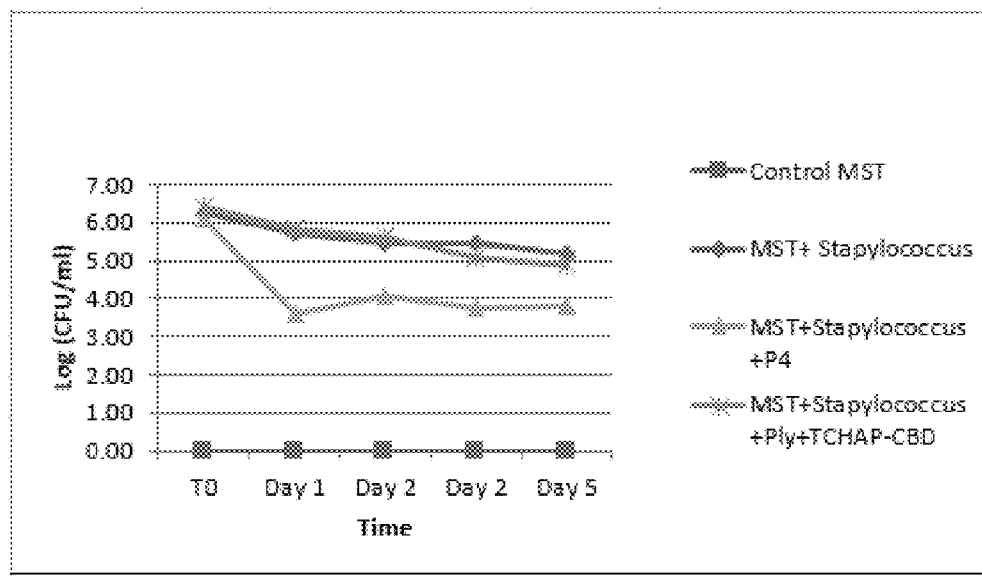
FIG. 13B is a graph showing the effectiveness of a combination of endolysins from two different bacteriophage against *Staphylococcus* in moist smokeless tobacco (MST) over 7 days in the fiberboard can.

Moist smokeless tobacco (MST) was inoculated with *Staphylococcus* sp. at a final concentration of $1.81 \times 10^6$ cfu/g (log 6.26). Bacteriophage against *Staphylococcus* as described herein was added to tobacco at a final concentration of $1 \times 10^{11}$ pfu/g (log 11). The tobacco was mixed for three minutes on medium speed using a kitchen aid mixer to ensure complete mixing and contact of the bacteria and the phage. The endolysins from each of the bacteriophage against *Staphylococcus* described herein (referred to in Table 2 as "Ply"+"TCHAP-CBD", which correspond to SEQ ID NOs: 6 and 8, respectively) were added to the tobacco at a final concentration of 120 μg/g (total). The tobacco was mixed for three minutes on medium speed using a kitchen aid mixer to ensure complete mixing and contact of the bacteria and the endolysin. The tobacco samples were monitored for growth of *Staphylococcus* for 7 days after packing in fiberboard cans. Results demonstrated that *Staphylococcus* was inhibited by the bacteriophage and endolysin over 7 days in the fiberboard can. See Table 3 and FIG. 13B.

TABLE 3

| Sample | Sample Point | Dilution | Plate 1 | Plate 2 | CFU/g | Log |
|---|---|---|---|---|---|---|
| Control MST | T0 | 10 | 0 | 0 | 0.00E+00 | 0.00 |
| MST + *Staphylococcus* | T0 | 1000 | 94 | 87 | 1.81E+06 | 6.26 |
| MST + *Staphylococcus* + P4 | T0 | 1000 | 60 | 66 | 1.26E+06 | 6.10 |
| MST + *Staphylococcus* + Ply + TCHAP-CBD | T0 | 10000 | 13 | 13 | 2.60E+06 | 6.41 |
| MST Control | Day 1 | 10 | 0 | 0 | 0.00E+00 | 0.00 |
| MST + *Staphylococcus* | Day 1 | 1000 | 27 | 26 | 5.30E+05 | 5.72 |
| MST + *Staphylococcus* + P4 | Day 1 | 100 | 2 | 2 | 4.00E+03 | 3.60 |
| MST + *Staphylococcus* + Ply + TCHAP-CBD | Day 1 | 1000 | 38 | 32 | 6.99E+05 | 5.84 |
| MST Control | Day 2 | 10 | 0 | 0 | 0.00E+00 | 0.00 |
| MST + *Staphylococcus* | Day 2 | 1000 | 14 | 15 | 2.90E+05 | 5.46 |
| MST + *Staphylococcus* + P4 | Day 2 | 100 | 3 | 9 | 1.20E+04 | 4.08 |
| MST + *Staphylococcus* + Ply + TCHAP-CBD | Day 2 | 1000 | 18 | 21 | 3.90E+05 | 5.59 |
| MST Control | Day 5 | 10 | 0 | 0 | 0.00E+00 | 0.00 |
| MST + *Staphylococcus* | Day 5 | 1000 | 15 | 13 | 2.80E+05 | 5.45 |
| MST + *Staphylococcus* + P4 | Day 5 | 100 | 2 | 4 | 6.00E+03 | 3.78 |
| MST + *Staphylococcus* + Ply + TCHAP-CBD | Day 5 | 100 | 64 | 60 | 1.24E+05 | 5.09 |
| MST Control | Day 7 | 10 | 0 | 0 | 0.00E+00 | 0.00 |
| MST + *Staphylococcus* | Day 7 | 1000 | 10 | 6 | 1.60E+05 | 5.20 |
| MST + *Staphylococcus* + P4 | Day 7 | 10 | 31 | 36 | 6.69E+03 | 3.83 |
| MST + *Staphylococcus* + Ply + TCHAP-CBD | Day 7 | 100 | 30 | 47 | 7.69E+04 | 4.89 |

It is to be understood that, while the methods and compositions of matter have been described herein in conjunction with a number of different aspects, the foregoing description of the various aspects is intended to illustrate and not limit the scope of the methods and compositions of matter. Other aspects, advantages, and modifications are within the scope of the following claims.

Disclosed are methods and compositions that can be used for, can be used in conjunction with, can be used in preparation for, or are products of the disclosed methods and compositions. These and other materials are disclosed herein, and it is understood that combinations, subsets, interactions, groups, etc. of these methods and compositions are disclosed. That is, while specific reference to each various individual and collective combinations and permutations of these compositions and methods may not be explicitly disclosed, each is specifically contemplated and described herein. For example, if a particular composition of matter or a particular method is disclosed and discussed and a number of compositions or methods are discussed, each and every combination and permutation of the compositions and the methods are specifically contemplated unless specifically indicated to the contrary. Likewise, any subset or combination of these is also specifically contemplated and disclosed.

What is claimed is:

1. A method for reducing the number of viable *Virgibacillus* bacteria cells in tobacco, comprising:

contacting tobacco with an amount of a composition effective for reducing the number of viable *Virgibacillus* bacteria cells in the tobacco, the composition comprising a polypeptide having at least 95% sequence identity to an amino acid sequence selected from the group consisting of SEQ ID NO: 4 and 12.

2. The method of claim 1, wherein the polypeptide has at least 99% sequence identity to an amino acid sequence selected from the group consisting of SEQ ID NO: 4 and 12.

3. The method of claim 1, wherein the polypeptide has an amino acid sequence selected from the group consisting of SEQ ID NO: 4 and 12.

4. The method of claim 1, wherein the polypeptide is encoded by a nucleic acid having at least 95% sequence identity to a nucleic acid sequence selected from the group consisting of SEQ ID NO: 3 and 11.

5. The method of claim 1, wherein the polypeptide is encoded by a nucleic acid having at least 99% sequence identity to a nucleic acid sequence selected from the group consisting of SEQ ID NO: 3 and 11.

6. The method of claim 1, wherein the polypeptide is encoded by a nucleic acid sequence selected from the group consisting of SEQ ID NO: 3 and 11.

7. The method of claim 1, wherein the polypeptide is isolated.

8. The method of claim 1, wherein the polypeptide is comprised within a bacteriophage.

9. The method of claim 1, wherein the tobacco is contacted with the composition prior to fermentation of the tobacco.

10. The method of claim 1, wherein the method reduces the level of tobacco-specific nitrosamines (TSNAs) in the tobacco.

11. The method of claim 1, wherein the polypeptide has at least 95% sequence identity to the amino acid sequence shown in SEQ ID NO:4.

12. The method of claim 1, wherein the polypeptide has at least 95% sequence identity to the amino acid sequence shown in SEQ ID NO:12.

13. The method of claim 1, wherein the polypeptide has at least 99% sequence identity to the amino acid sequence shown in SEQ ID NO:4.

14. The method of claim 1, wherein the polypeptide has at least 99% sequence identity to the amino acid sequence shown in SEQ ID NO:12.

15. The method of claim 1, wherein the polypeptide has the amino acid sequence shown in SEQ ID NO:4.

16. The method of claim 1, wherein the polypeptide has the amino acid sequence shown in SEQ ID NO:12.

17. The method of claim 1, wherein the polypeptide is encoded by a nucleic acid having at least 95% sequence identity to the nucleic acid sequence shown in SEQ ID NO:3.

18. The method of claim 1, wherein the polypeptide is encoded by a nucleic acid having at least 95% sequence identity to the nucleic acid sequence shown in SEQ ID NO:11.

19. The method of claim 1, wherein the polypeptide is encoded by a nucleic acid having at least 99% sequence identity to the nucleic acid sequence shown in SEQ ID NO:3.

20. The method of claim 1, wherein the polypeptide is encoded by a nucleic acid having at least 99% sequence identity to the nucleic acid sequence shown in SEQ ID NO:11.

21. The method of claim 1, wherein the polypeptide is encoded by a nucleic acid having the sequence shown in SEQ ID NO:3.

22. The method of claim 1, wherein the polypeptide is encoded by a nucleic acid having the sequence shown in SEQ ID NO:11.

\* \* \* \* \*

SEQUENCE LISTING

<160> NUMBER OF SEQ ID NOS: 12

<210> SEQ ID NO 1
<211> LENGTH: 1350
<212> TYPE: DNA
<213> ORGANISM: Artificial Sequence
<220> FEATURE:
<223> OTHER INFORMATION: Bacteriophage against Carnobacteriaceae sp.

<400> SEQUENCE: 1

```
atgattggtt acattttata cttacataga gaaaggaaag ggtttatgga aacatctcaa      60
aaaagaattc ccaaaaagaa aacctttttg acaattattg cgcttttat ctttatgact     120 tttgcttcat ttgcagcctt agcgaactca agtaaaataa ccgtggaagt tccagtactt     180
aatgttcgta ccggccctgg gctttcacac gatgtcacta ctcaagttta tgaagatcaa     240
gaattaaacg tattggaaga aaaagatcaa tggtacaaag tacgtttatc aaatgatcaa     300
attggctgga tagctagctg gttagttgaa gaacaagaag taacaactga aagtcagcgc     360
tttggacgta ttactgcgcc atcagtcaat gtaagacagt ttgcaacaac agattctagt     420
gtcctcaaca cagtaaatca agatgcacaa cttcaagtgt tattccaaca aggcgaatgg     480
actcaaattc aatataatga ccaagttggt tgggtacatt ctgattacat tcaacttatg     540
aatagctcag accaatctgt caatgttgaa tcaggacatg aagtaactat tggaaataca     600
gagacaaacg ttcgttcgca agcgactatt aattccaata taataaccac tgcatctgct     660
ggaactacat atccttactt aggtactgaa aacggttggc atatgattca gatgaatgat     720
ggttctacgg gctatgtttc aggtgaatgg actcaaataa atcctgtaac tacagcaaaa     780
gaccctcaaa ccagtccaca aacatctgca acaaatattt ctgaagcaac tattgttata     840
gatgcaggac atggcggaaa tgatccagga gctatagcct ctaacggtac gtatgaaaag     900
agtctcactt tagacactgc atatatatta caaagaaaat tagaaaatgc gggagctaat     960
gtgattatga ctcgttcaga cgactccttt gtatctctaa acaatcgtac tgtaacttct    1020
aaaactcatg gtgcagacgc gtttatcagt ttgcattatg attcaaataa taatgctagt    1080
gcaagtggta catcaacata ctactactca aaccaagaga aacaattagc gaatactgtt    1140
aatcaataca tgaattctta cggacaaatt ggaaataatg gtgtaaaaag aggaaattta    1200
catgtgctta gagagaattc tacaccgtca gtactttag aacttggttt tatgactaat    1260
tctcatgatt tagctcaaat tcaaacaggc tcatatcaag caactattgc tgatgcaatc    1320
tacttaggtt taactgagta tttcagctaa                                      1350
```

<210> SEQ ID NO 2
<211> LENGTH: 449
<212> TYPE: PRT

-continued

<213> ORGANISM: Artificial Sequence
<220> FEATURE:
<223> OTHER INFORMATION: Bacteriophage against Carnobacteriaceae sp.

<400> SEQUENCE: 2

```
Met Ile Gly Tyr Ile Leu Tyr Leu His Arg Glu Arg Lys Gly Phe Met
  1               5                  10                  15

Glu Thr Ser Gln Lys Arg Ile Pro Lys Lys Thr Phe Leu Thr Ile
             20                  25                  30

Ile Ala Leu Phe Ile Phe Met Thr Phe Ala Ser Phe Ala Ala Leu Ala
             35                  40                  45

Asn Ser Ser Lys Ile Thr Val Glu Val Pro Val Leu Asn Val Arg Thr
 50                  55                  60

Gly Pro Gly Leu Ser His Asp Val Thr Thr Gln Val Tyr Glu Asp Gln
 65                  70                  75                  80

Glu Leu Asn Val Leu Glu Glu Lys Asp Gln Trp Tyr Lys Val Arg Leu
                 85                  90                  95

Ser Asn Asp Gln Ile Gly Trp Ile Ala Ser Trp Leu Val Glu Glu Gln
                100                 105                 110

Glu Val Thr Thr Glu Ser Gln Arg Phe Gly Arg Ile Thr Ala Pro Ser
            115                 120                 125

Val Asn Val Arg Gln Phe Ala Thr Thr Asp Ser Ser Val Leu Asn Thr
130                 135                 140

Val Asn Gln Asp Ala Gln Leu Gln Val Leu Phe Gln Gln Gly Glu Trp
145                 150                 155                 160

Thr Gln Ile Gln Tyr Asn Asp Gln Val Gly Trp Val His Ser Asp Tyr
                165                 170                 175

Ile Gln Leu Met Asn Ser Ser Asp Gln Ser Val Asn Val Glu Ser Gly
                180                 185                 190

His Glu Val Thr Ile Gly Asn Thr Glu Thr Asn Val Arg Ser Gln Ala
            195                 200                 205

Thr Ile Asn Ser Asn Ile Ile Thr Thr Ala Ser Ala Gly Thr Thr Tyr
    210                 215                 220

Pro Tyr Leu Gly Thr Glu Asn Gly Trp His Met Ile Gln Met Asn Asp
225                 230                 235                 240

Gly Ser Thr Gly Tyr Val Ser Gly Glu Trp Thr Gln Ile Asn Pro Val
                245                 250                 255

Thr Thr Ala Lys Asp Pro Gln Thr Ser Pro Gln Thr Ser Ala Thr Asn
                260                 265                 270

Ile Ser Glu Ala Thr Ile Val Ile Asp Ala Gly His Gly Gly Asn Asp
            275                 280                 285

Pro Gly Ala Ile Ala Ser Asn Gly Thr Tyr Glu Lys Ser Leu Thr Leu
290                 295                 300

Asp Thr Ala Tyr Ile Leu Gln Arg Lys Leu Glu Asn Ala Gly Ala Asn
305                 310                 315                 320

Val Ile Met Thr Arg Ser Asp Asp Ser Phe Val Ser Leu Asn Asn Arg
                325                 330                 335

Thr Val Thr Ser Lys Thr His Gly Ala Asp Ala Phe Ile Ser Leu His
                340                 345                 350

Tyr Asp Ser Asn Asn Asn Ala Ser Ala Ser Gly Thr Ser Thr Tyr Tyr
            355                 360                 365

Tyr Ser Asn Gln Glu Lys Gln Leu Ala Asn Thr Val Asn Gln Tyr Met
370                 375                 380

Asn Ser Tyr Gly Gln Ile Gly Asn Asn Gly Val Lys Arg Gly Asn Leu
```

```
                385              390              395              400
His Val Leu Arg Glu Asn Ser Thr Pro Ser Val Leu Glu Leu Gly
                    405              410              415

Phe Met Thr Asn Ser His Asp Leu Ala Gln Ile Gln Thr Gly Ser Tyr
                420              425              430

Gln Ala Thr Ile Ala Asp Ala Ile Tyr Leu Gly Leu Thr Glu Tyr Phe
            435              440              445

Ser
```

<210> SEQ ID NO 3
<211> LENGTH: 1125
<212> TYPE: DNA
<213> ORGANISM: Artificial Sequence
<220> FEATURE:
<223> OTHER INFORMATION: Bacteriophage against Virgibacillus sp.

<400> SEQUENCE: 3

```
atgggttata ttatagacat ttcgcatcat caagatccag cgaaaataaa ttacgataaa      60
ttggcaaagc aagtagactt tgctattatt cgtacacaat atggatccag aacattagac     120
agtcattaca aaactcatca tcaggaactc caaaaacgtg gtgtaccgac tgctgcatat     180
gcatggatca ggggagtaag tgttaatgac atggaggtcg aagctactga cttttacaat     240
cggaccaaag aattcaatcc aacgttttgg tttttagatg tagaagaaaa atccatgtca     300
aacatgcgga aggcgctag tgcattctta ataagttac gtgacttagg tgctaaaaag     360
gtaggcatct atattgctaa ccacttatat gatagcttta atattgatgt aaatgaagcg     420
gatgcagtat ggattccaca ttatggctct aataacggta aacctaacag taagcctgat     480
catcctgctg acttgcatca atacacggac agaggtcgtt taaatggtta tagcggtaat     540
cttgacttaa accgcattat tagcgatgaa gatctatctt attttacgga tggacaagct     600
accaaaaaga aacatctag caacaaaaca tcaggtagca aatcaagcaa taaaatcact     660
ggtagcacat acaaagtaaa atcgggtgat acgttgtctg gtattgcaag cagagcaggc     720
acgacaacta aaaatcttca ggatattaat aacattagta accctgattt aataaaagtt     780
ggccaaacta ttaaattgaa agggtcgtca tctaataaaa ctggcggtac aacatacacc     840
gtaaaaagtg gagatacttt gagtggtatt gcttctaagt ttggtacgac caccaataaa     900
ttgcaggact taaacggtat tagtaatcct gacaagattt atgcaggaca gaaaattaag     960
gtaagtggtt cttcttcaag caaaaaatat catactgtta atcgggtga tactgttct    1020
gaattagccc aacaatttgg atccaatcag tcaaaaatta aagttggaa taacttagac    1080
agtaattata cgatttatgt tggacagaaa ttaagagtta agtaa                    1125
```

<210> SEQ ID NO 4
<211> LENGTH: 374
<212> TYPE: PRT
<213> ORGANISM: Artificial Sequence
<220> FEATURE:
<223> OTHER INFORMATION: Bacteriophage against Virgibacillus sp.

<400> SEQUENCE: 4

```
Met Gly Tyr Ile Ile Asp Ile Ser His His Gln Asp Pro Ala Lys Ile
  1               5                  10                  15

Asn Tyr Asp Lys Leu Ala Lys Gln Val Asp Phe Ala Ile Ile Arg Thr
             20                  25                  30

Gln Tyr Gly Ser Arg Thr Leu Asp Ser His Tyr Lys Thr His His Gln
         35                  40                  45
```

Glu Leu Gln Lys Arg Gly Val Pro Thr Ala Ala Tyr Ala Trp Ile Arg
 50                  55                  60

Gly Val Ser Val Asn Asp Met Glu Val Glu Ala Thr Asp Phe Tyr Asn
 65                  70                  75                  80

Arg Thr Lys Glu Phe Asn Pro Thr Phe Trp Phe Leu Asp Val Glu Glu
                 85                  90                  95

Lys Ser Met Ser Asn Met Arg Lys Gly Ala Ser Ala Phe Leu Asn Lys
                100                 105                 110

Leu Arg Asp Leu Gly Ala Lys Lys Val Gly Ile Tyr Ile Ala Asn His
                115                 120                 125

Leu Tyr Asp Ser Phe Asn Ile Asp Val Asn Glu Ala Asp Ala Val Trp
130                 135                 140

Ile Pro His Tyr Gly Ser Asn Asn Gly Lys Pro Asn Ser Lys Pro Asp
145                 150                 155                 160

His Pro Ala Asp Leu His Gln Tyr Thr Asp Arg Gly Arg Leu Asn Gly
                165                 170                 175

Tyr Ser Gly Asn Leu Asp Leu Asn Arg Ile Ile Ser Asp Glu Asp Leu
                180                 185                 190

Ser Tyr Phe Thr Asp Gly Gln Ala Thr Lys Lys Thr Ser Ser Asn
                195                 200                 205

Lys Thr Ser Gly Ser Lys Ser Ser Asn Lys Ile Thr Gly Ser Thr Tyr
210                 215                 220

Lys Val Lys Ser Gly Asp Thr Leu Ser Gly Ile Ala Ser Arg Ala Gly
225                 230                 235                 240

Thr Thr Thr Lys Asn Leu Gln Asp Ile Asn Asn Ile Ser Asn Pro Asp
                245                 250                 255

Leu Ile Lys Val Gly Gln Thr Ile Lys Leu Lys Gly Ser Ser Ser Asn
                260                 265                 270

Lys Thr Gly Gly Thr Thr Tyr Thr Val Lys Ser Gly Asp Thr Leu Ser
                275                 280                 285

Gly Ile Ala Ser Lys Phe Gly Thr Thr Thr Asn Lys Leu Gln Asp Leu
290                 295                 300

Asn Gly Ile Ser Asn Pro Asp Lys Ile Tyr Ala Gly Gln Lys Ile Lys
305                 310                 315                 320

Val Ser Gly Ser Ser Ser Lys Lys Tyr His Thr Val Lys Ser Gly
                325                 330                 335

Asp Thr Val Ser Glu Leu Ala Gln Gln Phe Gly Ser Asn Gln Ser Lys
                340                 345                 350

Ile Lys Ser Trp Asn Asn Leu Asp Ser Asn Tyr Thr Ile Tyr Val Gly
                355                 360                 365

Gln Lys Leu Arg Val Lys
370

<210> SEQ ID NO 5
<211> LENGTH: 4333
<212> TYPE: DNA
<213> ORGANISM: Artificial Sequence
<220> FEATURE:
<223> OTHER INFORMATION: Bacteriophage against Staphylococcus sp.

<400> SEQUENCE: 5
ctcgagaaat cataaaaaat ttatttgctt tgtgagcgga taacaattat aatagattca    60
attgtgagcg gataacaatt tcacacagaa ttcattaaag aggagaaatt aactatgaga   120
ggatcgcatc accatcacca tcacggatcc atgggcaaac agtatctggg taatggaat   180

```
ggtgtgccgg tttataccga ttatctgccg tatggcaccc gtcgtccggg tcgtaaactg      240
agcaccggta aaccggtgtt tgcagttgca catgataccg gcaatctgaa tagcaccgca      300
cagcagaatg tgaactttta tcgcaatacc tataacgaac agtttaacat tgccagcgca      360 cacttttcg tggatgataa agaatgcgtt atttgcatcc cgattgatga agttgcatat       420
catgttctgc ctgcagcacc gatggataat gcatggtatg gtcatgatgc caattatgca      480
gcatttggtg gtgaagcatg ttactttagc gacaaacaga aaagccagaa atccctggat      540
aacttttgtc gtgttatggc agcactgtgt aaaagctgga atatcaatcc ggttaatcgt      600
atgcctggtc atcagcagat tcagttcgat aaacaagatc cgggtaatct gctggcagca      660
tgtggttatg atcgtaatgc aatgcacatc attgataacc tggtcgtgaa atatatgcag      720
aacgccaata ccaaagtgaa aaagtacatc tacaactgga aggcaaatt taccgcacac       780 aaagataacg atgatccgat tgttgttcgt accacaccgg gtatgaatgg caaaattgtt      840
gaaaaaaaca gctggatcaa accgggtgaa tatgttccgt ttgatcagat tatcaaaaaa      900
gacggttatt ggtggctgcg cttcaaatat gtacagaaag gttccagcaa aaacgacttc      960
tatattccga ttggcaaaat cgaagaaaaa cacgaacgca ttaaaaacga aaaaaacctg     1020
tggggcaaac tggaagtgga ataagtcgac ctgcagccaa gcttaattag ctgagcttgg     1080
actcctgttg atagatccag taatgacctc agaactccat ctggatttgt tcagaacgct     1140
cggttgccgc cgggcgtttt ttattggtga aatccaagc tagcttggcg agattttcag      1200
gagctaagga agctaaaatg gagaaaaaaa tcactggata taccaccgtt gatatatccc     1260
aatggcatcg taaagaacat tttgaggcat ttcagtcagt tgctcaatgt acctataacc     1320
agaccgttca gctggatatt acggcctttt taaagaccgt aaagaaaaat aagcacaagt     1380
tttatccggc ctttattcac attcttgccc gcctgatgaa tgctcatccg gaatttcgta     1440
tggcaatgaa agacggtgag ctggtgatat gggatagtgt tcacccttgt tacaccgttt     1500
tccatgagca aactgaaacg ttttcatcgc tctggagtga ataccacgac gatttccggc     1560
agtttctaca catatattcg caagatgtgg cgtgttacgg tgaaaacctg gcctatttcc     1620
ctaaagggtt tattgagaat atgttttcg tctcagccaa tccctgggtg agtttcacca      1680
gttttgattt aaacgtggcc aatatggaca acttcttcgc ccccgttttc accatgggca     1740
aatattatac gcaaggcgac aaggtgctga tgccgctggc gattcaggtt catcatgccg     1800
tttgtgatgg cttccatgtc ggcagaatgc ttaatgaatt acaacagtac tgcgatgagt     1860
ggcagggcgg ggcgtaattt ttttaaggca gttattggtg cccttaaacg cctgggtaa      1920 tgactctcta gcttgaggca tcaaataaaa cgaaaggctc agtcgaaaga ctgggccttt     1980
cgttttatct gttgtttgtc ggtgaacgct ctcctgagta ggacaaatcc gccctctaga     2040
gctgcctcgc gcgtttcggt gatgacggtg aaaacctctg acacatgcag ctcccggaga     2100
cggtcacagc ttgtctgtaa gcggatgccg ggagcagaca agcccgtcag ggcgcgtcag     2160
cgggtgttgg cgggtgtcgg ggcgcagcca tgacccagtc acgtagcgat agcggagtgt     2220
atactggctt aactatgcgg catcagagca gattgtactg agagtgcacc atatgcggtg     2280
tgaaataccg cacagatgcg taaggagaaa ataccgcatc aggcgctctt ccgcttcctc     2340
gctcactgac tcgctgcgct cggtcgttcg gctgcggcga gcggtatcag ctcactcaaa     2400
ggcggtaata cggttatcca cagaatcagg ggataacgca ggaaagaaca tgtgagcaaa     2460
aggccagcaa aaggccagga accgtaaaaa ggccgcgttg ctggcgtttt tccataggct     2520
```

```
ccgccccct   gacgagcatc   acaaaaatcg   acgctcaagt   cagaggtggc   gaaacccgac      2580
aggactataa   agataccagg   cgtttccccc   tggaagctcc   ctcgtgcgct   ctcctgttcc      2640
gaccctgccg   cttaccggat   acctgtccgc   ctttctccct   tcgggaagcg   tggcgctttc      2700
tcatagctca   cgctgtaggt   atctcagttc   ggtgtaggtc   gttcgctcca   agctgggctg      2760
tgtgcacgaa   ccccccgttc   agcccgaccg   ctgcgcctta   tccggtaact   atcgtcttga      2820
gtccaacccg   gtaagacacg   acttatcgcc   actggcagca   gccactggta   acaggattag      2880
cagagcgagg   tatgtaggcg   gtgctacaga   gttcttgaag   tggtggccta   actacggcta      2940
cactagaagg   acagtatttg   gtatctgcgc   tctgctgaag   ccagttacct   tcggaaaaag      3000
agttggtagc   tcttgatccg   gcaaacaaac   caccgctggt   agcggtggtt   ttttttgtttg     3060 caagcagcag   attacgcgca   gaaaaaaagg   atctcaagaa   gatcctttga   tcttttctac      3120
ggggtctgac   gctcagtgga   acgaaaactc   acgttaaggg   attttggtca   tgagattatc      3180
aaaaaggatc   ttcacctaga   tccttttaaa   ttaaaaatga   agttttaaat   caatctaaag      3240
tatatatgag   taaacttggt   ctgacagtta   ccaatgctta   atcagtgagg   cacctatctc      3300
agcgatctgt   ctatttcgtt   catccatagt   tgcctgactc   cccgtcgtgt   agataactac      3360
gatacgggag   ggcttaccat   ctggccccag   tgctgcaatg   ataccgcgag   acccacgctc      3420
accggctcca   gatttatcag   caataaacca   gccagccgga   agggccgagc   gcagaagtgg      3480
tcctgcaact   ttatccgcct   ccatccagtc   tattaattgt   tgccgggaag   ctagagtaag      3540
tagttcgcca   gttaatagtt   tgcgcaacgt   tgttgccatt   gctacaggca   tcgtggtgtc      3600
acgctcgtcg   tttggtatgg   cttcattcag   ctccggttcc   caacgatcaa   ggcgagttac      3660
atgatccccc   atgttgtgca   aaaaagcggt   tagctccttc   ggtcctccga   tcgttgtcag      3720
aagtaagttg   gccgcagtgt   tatcactcat   ggttatggca   gcactgcata   attctcttac      3780
tgtcatgcca   tccgtaagat   gcttttctgt   gactggtgag   tactcaacca   agtcattctg      3840
agaatagtgt   atgcggcgac   cgagttgctc   ttgcccggcg   tcaatacggg   ataataccgc      3900
gccacatagc   agaactttaa   aagtgctcat   cattggaaaa   cgttcttcgg   ggcgaaaact      3960
ctcaaggatc   ttaccgctgt   tgagatccag   ttcgatgtaa   cccactcgtg   cacccaactg      4020
atcttcagca   tcttttactt   tcaccagcgt   ttctgggtga   gcaaaaacag   gaaggcaaaa      4080
tgccgcaaaa   aagggaataa   gggcgacacg   gaaatgttga   atactcatac   tcttcctttt      4140
tcaatattat   tgaagcattt   atcagggtta   ttgtctcatg   agcggataca   tatttgaatg      4200
tatttagaaa   aataaacaaa   taggggttcc   gcgcacattt   ccccgaaaag   tgccacctga      4260
cgtctaagaa   accattatta   tcatgacatt   aacctataaa   aataggcgta   tcacgaggcc      4320
ctttcgtctt   cac                                                                4333
```

<210> SEQ ID NO 6
<211> LENGTH: 309
<212> TYPE: PRT
<213> ORGANISM: Artificial Sequence
<220> FEATURE:
<223> OTHER INFORMATION: Bacteriophage against Staphylococcus sp.

<400> SEQUENCE: 6

Met Arg Gly Ser His His His His His His Gly Ser Met Gly Lys Gln
 1               5                  10                  15

Tyr Leu Gly Lys Trp Asn Gly Val Pro Val Tyr Thr Asp Tyr Leu Pro
             20                  25                  30

Tyr Gly Thr Arg Arg Pro Gly Arg Lys Leu Ser Thr Gly Lys Pro Val

```
                35                  40                  45
Phe Ala Val Ala His Asp Thr Gly Asn Leu Asn Ser Thr Ala Gln Gln
 50                  55                  60
Asn Val Asn Phe Tyr Arg Asn Thr Tyr Asn Glu Gln Phe Asn Ile Ala
 65                  70                  75                  80
Ser Ala His Phe Phe Val Asp Asp Lys Glu Cys Val Ile Cys Ile Pro
                 85                  90                  95
Ile Asp Glu Val Ala Tyr His Val Leu Pro Ala Ala Pro Met Asp Asn
                100                 105                 110
Ala Trp Tyr Gly His Asp Ala Asn Tyr Ala Ala Phe Gly Gly Glu Ala
                115                 120                 125
Cys Tyr Phe Ser Asp Lys Gln Lys Ser Gln Lys Ser Leu Asp Asn Phe
                130                 135                 140
Cys Arg Val Met Ala Ala Leu Cys Lys Ser Trp Asn Ile Asn Pro Val
145                 150                 155                 160
Asn Arg Met Pro Gly His Gln Gln Ile Gln Phe Asp Lys Gln Asp Pro
                165                 170                 175
Gly Asn Leu Leu Ala Ala Cys Gly Tyr Asp Arg Asn Ala Met His Ile
                180                 185                 190
Ile Asp Asn Leu Val Val Lys Tyr Met Gln Asn Ala Asn Thr Lys Val
                195                 200                 205
Lys Lys Tyr Ile Tyr Asn Trp Lys Gly Lys Phe Thr Ala His Lys Asp
210                 215                 220
Asn Asp Asp Pro Ile Val Val Arg Thr Thr Pro Gly Met Asn Gly Lys
225                 230                 235                 240
Ile Val Glu Lys Asn Ser Trp Ile Lys Pro Gly Glu Tyr Val Pro Phe
                245                 250                 255
Asp Gln Ile Ile Lys Lys Asp Gly Tyr Trp Trp Leu Arg Phe Lys Tyr
                260                 265                 270
Val Gln Lys Gly Ser Ser Lys Asn Asp Phe Tyr Ile Pro Ile Gly Lys
                275                 280                 285
Ile Glu Glu Lys His Glu Arg Ile Lys Asn Lys Asn Leu Trp Gly
                290                 295                 300
Lys Leu Glu Val Glu
305

<210> SEQ ID NO 7
<211> LENGTH: 4393
<212> TYPE: DNA
<213> ORGANISM: Artificial Sequence
<220> FEATURE:
<223> OTHER INFORMATION: Bacteriophage against Staphylococcus sp.

<400> SEQUENCE: 7
ctcgagaaat cataaaaaat ttatttgctt tgtgagcgga taacaattat aatagattca      60
attgtgagcg gataacaatt tcacacagaa ttcattaaag aggagaaatt aactatgaga     120
ggatcgcatc accatcacca tcacggatcc ggtaaaagcg ttaaaccgaa tggtaaaagt     180
ggtaaagtga ttggtggtaa ttggacctgg aacagctgcc gcagaaaata caaagatgca     240
attaccctgc ctcgcttcaa acatagttat gttcagaaac gcataatcg ttttgttccg      300 accggcaata ccgtcagtg taccgaactg acctggggtt atatgagcca gctgtggggt      360
aaagaacagc gcaggatga tggtcagatt accaatggtc agcgtgtttg gtatgtgtat     420
cagaaactgg gtgcaaaaac cacccataat ccgaccgttg gttatggttt tagcagcaaa     480
```

```
ccgccttatg ttaatgcagc aattcagggt attggtcata ccggtgttgt tgttgcagtt      540
tttgatgatg gtagctttct gatttgcaat tggaatgttc cgccttattg ggcaccgagc      600
cgtgttgata tgtttagcct gattgatggt gttccgcata atgccggtga taacattgtg      660
ttttttagcg gtattaaagc aggcaccacc gtgaaaaaag aaaccgccaa aaaaagcgca      720
agcaaaacac cggcaccgaa aaaaaagca accctgaaag tttcgaaaaa ccacattgag       780
ctcgccaata ccaaagtgaa aaagtacatc tacaactgga aaggcaaatt taccgcacac     840
aaagataacg atgatccgat tgttgttcgt accacaccgg gtatgaatgg caaaattgtt     900
gaaaaaaaca gctggatcaa accgggtgaa tatgttccgt ttgatcagat tatcaaaaaa     960
gacggttatt ggtggctgcg cttcaaatat gtacagaaag gttccagcaa aaacgacttc    1020
tatattccga ttggcaaaat cgaagaaaaa cacgaacgca ttaaaaacga aaaaaacctg    1080
tggggcaaac tggaagtgga ataagtcgac ctgcagccaa gcttaattag ctgagcttgg    1140
actcctgttg atagatccag taatgacctc agaactccat ctggatttgt tcagaacgct    1200
cggttgccgc cgggcgtttt ttattggtga aatccaagc tagcttggcg agattttcag     1260
gagctaagga agctaaaatg gagaaaaaaa tcactggata taccaccgtt gatatatccc    1320
aatggcatcg taaagaacat tttgaggcat ttcagtcagt tgctcaatgt acctataacc    1380
agaccgttca gctggatatt acggcctttt aaagaccgt aaagaaaaat aagcacaagt     1440
tttatccggc ctttattcac attcttgccc gcctgatgaa tgctcatccg gaatttcgta    1500
tggcaatgaa agacggtgag ctggtgatat gggatagtgt tcacccttgt tacaccgttt    1560
tccatgagca aactgaaacg ttttcatcgc tctggagtga ataccacgac gatttccggc    1620
agtttctaca catatattcg caagatgtgg cgtgttacgg tgaaaacctg gcctatttcc    1680
ctaaagggtt tattgagaat atgttttcg tctcagccaa tccctgggtg agtttcacca    1740
gttttgattt aaacgtggcc aatatggaca acttcttcgc cccgttttc accatgggca    1800 aatattatac gcaaggcgac aaggtgctga tgccgctggc gattcaggtt catcatgccg   1860
tttgtgatgg cttccatgtc ggcagaatgc ttaatgaatt acaacagtac tgcgatgagt   1920
ggcagggcgg ggcgtaattt ttttaaggca gttattggtg cccttaaacg cctggggtaa   1980
tgactctcta gcttgaggca tcaaataaaa cgaaaggctc agtcgaaaga ctgggccttt   2040
cgttttatct gttgtttgtc ggtgaacgct ctcctgagta ggacaaatcc gccctctaga   2100
gctgcctcgc gcgtttcggt gatgacggtg aaaacctctg acacatgcag ctcccggaga   2160
cggtcacagc ttgtctgtaa gcggatgccg ggagcagaca gcccgtcag ggcgcgtcag     2220 cgggtgttgg cgggtgtcgg ggcgcagcca tgacccagtc acgtagcgat agcggagtgt   2280
atactggctt aactatgcgg catcagagca gattgtactg agagtgcacc atatgcggtg   2340
tgaaataccg cacagatgcg taaggagaaa ataccgcatc aggcgctctt ccgcttcctc   2400
gctcactgac tcgctgcgct cggtcgttcg gctgcggcga gcggtatcag ctcactcaaa   2460
ggcggtaata cggttatcca cagaatcagg ggataacgca ggaaagaaca tgtgagcaaa   2520
aggccagcaa aaggccagga accgtaaaaa ggccgcgttg ctggcgtttt tccataggct   2580
ccgcccccct gacgagcatc acaaaaatcg acgctcaagt cagaggtggc gaaacccgac   2640
aggactataa agataccagg cgtttccccc tggaagctcc ctcgtgcgct ctcctgttcc   2700
gaccctgccg cttaccggat acctgtccgc ctttctccct tcgggaagcg tggcgctttc   2760
tcatagctca cgctgtaggt atctcagttc ggtgtaggtc gttcgctcca agctgggctg   2820
tgtgcacgaa ccccccgttc agcccgaccg ctgcgcctta tccggtaact atcgtcttga   2880
```

```
gtccaacccg gtaagacacg acttatcgcc actggcagca gccactggta acaggattag    2940
cagagcgagg tatgtaggcg gtgctacaga gttcttgaag tggtggccta actacggcta    3000
cactagaagg acagtatttg gtatctgcgc tctgctgaag ccagttacct tcggaaaaag    3060
agttggtagc tcttgatccg gcaaacaaac caccgctggt agcggtggtt ttttttgtttg   3120 caagcagcag attacgcgca gaaaaaaagg atctcaagaa gatcctttga tcttttctac    3180
ggggtctgac gctcagtgga acgaaaactc acgttaaggg attttggtca tgagattatc    3240
aaaaaggatc ttcacctaga tccttttaaa ttaaaaatga agttttaaat caatctaaag    3300
tatatatgag taaacttggt ctgacagtta ccaatgctta atcagtgagg cacctatctc    3360
agcgatctgt ctatttcgtt catccatagt tgcctgactc ccgtcgtgt agataactac      3420 gatacgggag ggcttaccat ctggccccag tgctgcaatg ataccgcgag acccacgctc    3480
accggctcca gatttatcag caataaacca gccagccgga agggccgagc gcagaagtgg    3540
tcctgcaact ttatccgcct ccatccagtc tattaattgt tgccgggaag ctagagtaag    3600
tagttcgcca gttaatagtt tgcgcaacgt tgttgccatt gctacaggca tcgtggtgtc    3660
acgctcgtcg tttggtatgg cttcattcag ctccggttcc caacgatcaa ggcgagttac    3720
atgatccccc atgttgtgca aaaaagcggt tagctccttc ggtcctccga tcgttgtcag    3780
aagtaagttg gccgcagtgt tatcactcat ggttatggca gcactgcata attctcttac    3840
tgtcatgcca tccgtaagat gcttttctgt gactggtgag tactcaacca agtcattctg    3900
agaatagtgt atgcggcgac cgagttgctc ttgcccggcg tcaatacggg ataataccgc    3960
gccacatagc agaactttaa aagtgctcat cattggaaaa cgttcttcgg ggcgaaaact    4020
ctcaaggatc ttaccgctgt tgagatccag ttcgatgtaa cccactcgtg cacccaactg    4080
atcttcagca tcttttactt tcaccagcgt ttctgggtga gcaaaaacag gaaggcaaaa    4140
tgccgcaaaa aagggaataa gggcgacacg gaaatgttga atactcatac tcttcctttt    4200
tcaatattat tgaagcattt atcagggtta ttgtctcatg agcggataca tatttgaatg    4260
tatttagaaa aataaacaaa tagggggttcc gcgcacattt ccccgaaaag tgccacctga    4320
cgtctaagaa accattatta tcatgacatt aacctataaa aataggcgta tcacgaggcc    4380 ctttcgtcttt cac                                                      4393
```

<210> SEQ ID NO 8
<211> LENGTH: 329
<212> TYPE: PRT
<213> ORGANISM: Artificial Sequence
<220> FEATURE:
<223> OTHER INFORMATION: Bacteriophage against Staphylococcus sp.

<400> SEQUENCE: 8

Met Arg Gly Ser His His His His His His Gly Ser Gly Lys Ser Val
1               5                   10                  15

Lys Pro Asn Gly Lys Ser Gly Lys Val Ile Gly Asn Trp Thr Trp
            20                  25                  30

Glu Gln Leu Pro Gln Lys Tyr Lys Asp Ala Ile Thr Leu Pro Arg Phe
        35                  40                  45

Lys His Ser Tyr Val Gln Lys Pro His Asn Arg Phe Val Pro Thr Gly
    50                  55                  60

Asn Thr Gly Gln Cys Thr Glu Leu Thr Trp Gly Tyr Met Ser Gln Leu
65                  70                  75                  80

Trp Gly Lys Glu Gln Pro Gln Asp Asp Gly Gln Ile Thr Asn Gly Gln

```
                    85                  90                  95
Arg Val Trp Tyr Val Tyr Gln Lys Leu Gly Ala Lys Thr Thr His Asn
            100                 105                 110

Pro Thr Val Gly Tyr Gly Phe Ser Ser Lys Pro Pro Tyr Val Asn Ala
            115                 120                 125

Ala Ile Gln Gly Ile Gly His Thr Gly Val Val Ala Val Phe Asp
            130                 135                 140

Asp Gly Ser Phe Leu Ile Cys Asn Trp Asn Val Pro Pro Tyr Trp Ala
145                 150                 155                 160

Pro Ser Arg Val Asp Met Phe Ser Leu Ile Asp Gly Val Pro His Asn
            165                 170                 175

Ala Gly Asp Asn Ile Val Phe Phe Ser Gly Ile Lys Ala Gly Thr Thr
            180                 185                 190

Val Lys Lys Glu Thr Ala Lys Lys Ser Ala Ser Lys Thr Pro Ala Pro
            195                 200                 205

Lys Lys Lys Ala Thr Leu Lys Val Ser Lys Asn His Ile Glu Leu Ala
            210                 215                 220

Asn Thr Lys Val Lys Lys Tyr Ile Tyr Asn Trp Lys Gly Lys Phe Thr
225                 230                 235                 240

Ala His Lys Asp Asn Asp Pro Ile Val Val Arg Thr Thr Pro Gly
            245                 250                 255

Met Asn Gly Lys Ile Val Glu Lys Asn Ser Trp Ile Lys Pro Gly Glu
            260                 265                 270

Tyr Val Pro Phe Asp Gln Ile Ile Lys Lys Asp Gly Tyr Trp Trp Leu
            275                 280                 285

Arg Phe Lys Tyr Val Gln Lys Gly Ser Ser Lys Asn Asp Phe Tyr Ile
            290                 295                 300

Pro Ile Gly Lys Ile Glu Glu Lys His Glu Arg Ile Lys Asn Glu Lys
305                 310                 315                 320

Asn Leu Trp Gly Lys Leu Glu Val Glu
                325

<210> SEQ ID NO 9
<211> LENGTH: 4381
<212> TYPE: DNA
<213> ORGANISM: Artificial Sequence
<220> FEATURE:
<223> OTHER INFORMATION: Bacteriophage against Carnobacteriaceae sp.

<400> SEQUENCE: 9
ctcgagaaat cataaaaaat ttatttgctt tgtgagcgga taacaattat aatagattca      60
attgtgagcg gataacaatt tcacacagaa ttcattaaag aggagaaatt aactatgaga     120
ggatcgcatc accatcacca tcacggatcc atgaccggta ttatgaatcc gcaagaagtt     180
gaggaactga aaataacgt tctgagcaaa gccaaaagct atgttggcac caagagggt      240 gatgcaaaac ataagaact gatcaatcag tataacgccg ttaaaccgct gccggttggt     300
tatccggtga atataccga tgattggtgt gcagcatttg tgaccgttat ggtgatctg      360 accaatgtga gcgaatatat tggtcgtgaa tgtggtgttc agcgctttgt gaaaatcttc     420
aaaaacaaag gtatttggcg tggtctggca aaccgcagg caggcgatat tattgtgttt     480
gattggcaga aaaatggctg gcagatcat attggttttg tggaaaaagt ggacggcaac     540
aaaattacca ccattgaagg taataccagc aaacaggttg cacgtcgtac ctatgcatgg     600
aatgattggc gtgttagcgg ttatgcacgt ccgaaatatc cgagcggcac caataccacc     660
```

```
aataaaagca ttaatgaagt gacccatgaa gtgctgaaca aaaaatgggg taatggcaat    720
gaacgtaaac agcgtctgac ccaggcaggt tataatgcac aggcagttca gaatgaagtt    780
aatcgtctgc tgaaaaccaa aggcaatctg aaaagcaatg aaacgattgc caaagaggtt    840
attgcaaaac agtggggcaa tggtgaaacc cgcaaacaac gcctgaccga agccggttat    900
gattacaatg caattcagaa agccgttaac cagctgatga atccaaaaa cagccatctg     960 aaaacaaacg aaaccgtggc aaaagaggtg attcagcaga atggggcaa cggtcagaca    1020 cggaaacagc ggctgacgga agcaggctat gactatgacg ccgttcagaa aattgttaac    1080
agcctgatct aagtcgacct gcagccaagc ttaattagct gagcttggac tcctgttgat    1140
agatccagta atgacctcag aactccatct ggatttgttc agaacgctcg gttgccgccg    1200 ggcgttttt attggtgaga atccaagcta gcttggcgag attttcagga gctaaggaag    1260
ctaaaatgga gaaaaaatc actggatata ccaccgttga tatatcccaa tggcatcgta    1320
aagaacattt tgaggcattt cagtcagttg ctcaatgtac ctataaccag accgttcagc    1380
tggatattac ggccttttta aagaccgtaa agaaaaataa gcacaagttt tatccggcct    1440
ttattcacat tcttgcccgc ctgatgaatg ctcatccgga atttcgtatg gcaatgaaag    1500
acggtgagct ggtgatatgg gatagtgttc acccttgtta caccgttttc catgagcaaa    1560
ctgaaacgtt ttcatcgctc tggagtgaat accacgacga tttccggcag tttctacaca    1620
tatattcgca agatgtggcg tgttacggtg aaaacctggc ctatttccct aaagggttta    1680
ttgagaatat gttttccgtc tcagccaatc cctgggtgag tttcaccagt tttgatttaa    1740
acgtggccaa tatggacaac ttcttcgccc ccgttttcac catgggcaaa tattatacgc    1800
aaggcgacaa ggtgctgatg ccgctggcga ttcaggttca tcatgccgtt tgtgatggct    1860
tccatgtcgg cagaatgctt aatgaattac aacagtactg cgatgagtgg cagggcgggg    1920 cgtaatttt ttaaggcagt tattggtgcc cttaaacgcc tggggtaatg actctctagc    1980
ttgaggcatc aaataaaacg aaaggctcag tcgaaagact gggcctttcg ttttatctgt    2040
tgtttgtcgg tgaacgctct cctgagtagg acaaatccgc cctctagagc tgcctcgcgc    2100
gtttcggtga tgacggtgaa aacctctgac acatgcagct cccggagacg gtcacagctt    2160
gtctgtaagc ggatgccggg agcagacaag cccgtcaggg cgcgtcagcg ggtgttggcg    2220
ggtgtcgggg cgcagccatg acccagtcac gtagcgatag cggagtgtat actggcttaa    2280
ctatgcggca tcagagcaga ttgtactgag agtgcaccat atgcggtgtg aaataccgca    2340
cagatgcgta aggagaaaat accgcatcag gcgctcttcc gcttcctcgc tcactgactc    2400
gctgcgctcg gtcgttcggc tgcggcgagc ggtatcagct cactcaaagg cggtaatacg    2460
gttatccaca gaatcagggg ataacgcagg aaagaacatg tgagcaaaag gccagcaaaa    2520
ggccaggaac cgtaaaaagg ccgcgttgct ggcgtttttc cataggctcc gcccccctga    2580
cgagcatcac aaaaatcgac gctcaagtca gaggtggcga aacccgacag gactataaag    2640
ataccaggcg tttccccctg gaagctccct cgtgcgctct cctgttccga ccctgccgct    2700
taccggatac ctgtccgcct ttctcccttc gggaagcgtg gcgctttctc atagctcacg    2760
ctgtaggtat ctcagttcgg tgtaggtcgt tcgctccaag ctgggctgtg tgcacgaacc    2820
ccccgttcag cccgaccgct gcgccttatc cggtaactat cgtcttgagt ccaacccggt    2880
aagacacgac ttatcgccac tggcagcagc cactggtaac aggattagca gagcgaggta    2940
tgtaggcggt gctacagagt tcttgaagtg gtggcctaac tacggctaca ctagaaggac    3000
agtatttggt atctgcgctc tgctgaagcc agttaccttc ggaaaaagag ttggtagctc    3060
```

```
ttgatccggc aaacaaacca ccgctggtag cggtggtttt tttgtttgca agcagcagat    3120
tacgcgcaga aaaaaggat ctcaagaaga tcctttgatc ttttctacgg ggtctgacgc    3180
tcagtggaac gaaaactcac gttaagggat tttggtcatg agattatcaa aaaggatctt    3240
cacctagatc cttttaaatt aaaaatgaag ttttaaatca atctaaagta tatatgagta    3300
aacttggtct gacagttacc aatgcttaat cagtgaggca cctatctcag cgatctgtct    3360
atttcgttca tccatagttg cctgactccc cgtcgtgtag ataactacga tacgggaggg    3420
cttaccatct ggccccagtg ctgcaatgat accgcgagac ccacgctcac cggctccaga    3480
tttatcagca ataaaccagc cagccggaag ggccgagcgc agaagtggtc ctgcaacttt    3540
atccgcctcc atccagtcta ttaattgttg ccgggaagct agagtaagta gttcgccagt    3600
taatagtttg cgcaacgttg ttgccattgc tacaggcatc gtggtgtcac gctcgtcgtt    3660
tggtatggct tcattcagct ccggttccca acgatcaagg cgagttacat gatccccat    3720 gttgtgcaaa aaagcggtta gctccttcgg tcctccgatc gttgtcagaa gtaagttggc    3780
cgcagtgtta tcactcatgg ttatggcagc actgcataat tctcttactg tcatgccatc    3840
cgtaagatgc ttttctgtga ctggtgagta ctcaaccaag tcattctgag aatagtgtat    3900
gcggcgaccg agttgctctt gcccggcgtc aatacgggat aataccgcgc cacatagcag    3960
aactttaaaa gtgctcatca ttggaaaacg ttcttcgggg cgaaaactct caaggatctt    4020
accgctgttg agatccagtt cgatgtaacc cactcgtgca cccaactgat cttcagcatc    4080
ttttactttc accagcgttt ctgggtgagc aaaaacagga aggcaaaatg ccgcaaaaaa    4140
gggaataagg gcgacacgga aatgttgaat actcatactc ttccttttc aatattattg    4200 aagcatttat cagggttatt gtctcatgag cggatacata tttgaatgta tttagaaaaa    4260
taaacaaata ggggttccgc gcacatttcc ccgaaaagtg ccacctgacg tctaagaaac    4320
cattattatc atgacattaa cctataaaaa taggcgtatc acgaggccct ttcgtcttca    4380
c                                                                   4381
```

<210> SEQ ID NO 10  
<211> LENGTH: 325  
<212> TYPE: PRT  
<213> ORGANISM: Artificial Sequence  
<220> FEATURE:  
<223> OTHER INFORMATION: Bacteriophage against Carnobacteriaceae sp.

<400> SEQUENCE: 10

Met Arg Gly Ser His His His His His His Gly Ser Met Thr Gly Ile
1               5                   10                  15

Met Asn Pro Gln Glu Val Glu Glu Leu Lys Asn Asn Val Leu Ser Lys
            20                  25                  30

Ala Lys Ser Tyr Val Gly Thr Gln Glu Gly Asp Ala Lys His Lys Glu
        35                  40                  45

Leu Ile Asn Gln Tyr Asn Ala Val Lys Pro Leu Pro Val Gly Tyr Pro
    50                  55                  60

Val Lys Tyr Thr Asp Asp Trp Cys Ala Ala Phe Val Thr Val Ile Gly
65                  70                  75                  80

Asp Leu Thr Asn Val Ser Glu Tyr Ile Gly Arg Glu Cys Gly Val Gln
                85                  90                  95

Arg Phe Val Lys Ile Phe Lys Asn Lys Gly Ile Trp Arg Gly Leu Ala
            100                 105                 110

Lys Pro Gln Ala Gly Asp Ile Ile Val Phe Asp Trp Gln Lys Asn Gly

```
                115                 120                 125
Trp Ala Asp His Ile Gly Phe Val Glu Lys Val Asp Gly Asn Lys Ile
    130                 135                 140

Thr Thr Ile Glu Gly Asn Thr Ser Lys Gln Val Ala Arg Arg Thr Tyr
145                 150                 155                 160

Ala Trp Asn Asp Trp Arg Val Ser Gly Tyr Ala Arg Pro Lys Tyr Pro
                165                 170                 175

Ser Gly Thr Asn Thr Thr Asn Lys Ser Ile Asn Glu Val Thr His Glu
            180                 185                 190

Val Leu Asn Lys Lys Trp Gly Asn Gly Asn Glu Arg Lys Gln Arg Leu
        195                 200                 205

Thr Gln Ala Gly Tyr Asn Ala Gln Ala Val Gln Asn Glu Val Asn Arg
    210                 215                 220

Leu Leu Lys Thr Lys Gly Asn Leu Lys Ser Asn Glu Thr Ile Ala Lys
225                 230                 235                 240

Glu Val Ile Ala Lys Gln Trp Gly Asn Gly Glu Thr Arg Lys Gln Arg
                245                 250                 255

Leu Thr Glu Ala Gly Tyr Asp Tyr Asn Ala Ile Gln Lys Ala Val Asn
            260                 265                 270

Gln Leu Met Lys Ser Lys Asn Ser His Leu Lys Thr Asn Glu Thr Val
        275                 280                 285

Ala Lys Glu Val Ile Gln Gln Lys Trp Gly Asn Gly Gln Thr Arg Lys
    290                 295                 300

Gln Arg Leu Thr Glu Ala Gly Tyr Asp Tyr Asp Ala Val Gln Lys Ile
305                 310                 315                 320

Val Asn Ser Leu Ile
                325

<210> SEQ ID NO 11
<211> LENGTH: 4560
<212> TYPE: DNA
<213> ORGANISM: Artificial Sequence
<220> FEATURE:
<223> OTHER INFORMATION: Bacteriophage against Virgibacillus sp.

<400> SEQUENCE: 11
ctcgagaaat cataaaaaat ttatttgctt tgtgagcgga taacaattat aatagattca      60
attgtgagcg gataacaatt tcacacagaa ttcattaaag aggagaaatt aactatgaga     120
ggatcgcatc accatcacca tcacggatcc atgggctata ttatcgatat cagccatcat     180
caagatccgg caaaaatcaa ctatgacaaa ctggcaaaac aggtggattt tgccattatt     240
cgtacccagt atggtagccg tacccctggat agccactata aaacccatca ccaagaactg     300
cagaaacgtg tgttccgac cgcagcctat gcatggattc gtggtgttag cgttaatgat     360
atggaagttg aagccaccga tttctataat cgcaccaaag aatttaaccc gaccttttgg     420
tttctggacg ttgaagaaaa aagcatgagc aatatgcgta aggtgcaagc gcatttctg     480 aataaactgc gtgatctggg tgcaaaaaaa gtgggtatct atattgccaa ccacctgtat     540
gatagcttta acattgatgt gaatgaagcc gatgcagttt ggattccgca ttatggtagc     600
aataatggta aaccgaatag caaaccggat catcctgccg atctgcatca gtataccgat     660
cgtggtcgtc tgaatggtta tagcggtaat ctggatctga accgtattat cagtgatgag     720
gatctgagct atttaccga tggtcaggca accaaaaaaa aaccagcag caataaaacc     780 agcggtagca aagcagcaa caaaatcacc ggttcaacct acaaagttaa agcggtgat     840
```

```
accctgagcg gtattgcaag ccgtgcaggc accaccacca aaaatctgca ggatattaac    900
aatatcagca acccggatct gattaaagtt ggccagacca ttaaactgaa aggcagcagc    960
tcaaataaaa ccggtggcac cacctatacc gttaaatcag gcgataccct gtcaggtatt   1020
gccagcaaat ttggtacaac cacaaacaaa ctgcaggacc tgaatggtat tagcaatccg   1080
gataaaatct atgccggtca gaaaatcaaa gttagcggta gtagctccag caaaaagtat   1140
cataccgtga aaagtggcga taccgtttca gaactggcac agcagtttgg tagtaatcag   1200
agcaaaatca aaagctggaa caatctggat tccaactata ccatttatgt gggtcagaaa   1260
ctgcgcgtga aataagtcga cctgcagcca agcttaatta gctgagcttg gactcctgtt   1320
gatagatcca gtaatgacct cagaactcca tctggatttg ttcagaacgc tcggttgccg   1380
ccgggcgttt tttattggtg agaatccaag ctagcttggc gagattttca ggagctaagg   1440
aagctaaaat ggagaaaaaa atcactggat ataccaccgt tgatatatcc caatggcatc   1500
gtaaagaaca ttttgaggca tttcagtcag ttgctcaatg tacctataac cagaccgttc   1560
agctggatat tacggccttt ttaaagaccg taaagaaaaa taagcacaag ttttatccgg   1620
cctttattca cattcttgcc cgcctgatga atgctcatcc ggaatttcgt atggcaatga   1680
aagacggtga gctggtgata tgggatagtg ttcacccttg ttacaccgtt ttccatgagc   1740
aaactgaaac gttttcatcg ctctggagtg aataccacga cgatttccgg cagtttctac   1800
acatatattc gcaagatgtg gcgtgttacg gtgaaaacct ggcctatttc cctaaagggt   1860
ttattgagaa tatgtttttc gtctcagcca atccctgggt gagtttcacc agttttgatt   1920
taaacgtggc caatatggac aacttcttcg cccccgtttt caccatgggc aaatattata   1980
cgcaaggcga caaggtgctg atgccgctgg cgattcaggt tcatcatgcc gtttgtgatg   2040
gcttccatgt cggcagaatg cttaatgaat tacaacagta ctgcgatgag tggcagggcg   2100
gggcgtaatt ttttttaaggc agttattggt gcccttaaac gcctggggta atgactctct   2160
agcttgaggc atcaaataaa acgaaaggct cagtcgaaag actgggcctt tcgttttatc   2220
tgttgtttgt cggtgaacgc tctcctgagt aggacaaatc cgccctctag agctgcctcg   2280
cgcgtttcgg tgatgacggt gaaaacctct gacacatgca gctcccggag acggtcacag   2340
cttgtctgta agcggatgcc gggagcagac aagcccgtca gggcgcgtca gcgggtgttg   2400
gcgggtgtcg gggcgcagcc atgacccagt cacgtagcga tagcggagtg tatactggct   2460
taactatgcg gcatcagagc agattgtact gagagtgcac catatgcggt gtgaaatacc   2520
gcacagatgc gtaaggagaa ataccgcat caggcgctct ccgcttcct cgctcactga   2580
ctcgctgcgc tcggtcgttc ggctgcggcg agcggtatca gctcactcaa aggcggtaat   2640
acggttatcc acagaatcag gggataacgc aggaaagaac atgtgagcaa aaggccagca   2700
aaaggccagg aaccgtaaaa aggccgcgtt gctggcgttt ttccataggc tccgcccccc   2760
tgacgagcat cacaaaaatc gacgctcaag tcagaggtgg cgaaacccga caggactata   2820
aagataccag gcgtttcccc ctggaagctc cctcgtgcgc tctcctgttc cgaccctgcc   2880
gcttaccgga tacctgtccg cctttctccc ttcgggaagc gtggcgcttt ctcatagctc   2940
acgctgtagg tatctcagtt cggtgtaggt cgttcgctcc aagctgggct gtgtgcacga   3000
accccccgtt cagcccgacc gctgcgcctt atccggtaac tatcgtcttg agtccaaccc   3060
ggtaagacac gacttatcgc cactggcagc agccactggt aacaggatta gcagagcgag   3120
gtatgtaggc ggtgctacag agttcttgaa gtggtggcct aactacggct acactagaag   3180
gacagtattt ggtatctgcg ctctgctgaa gccagttacc ttcggaaaaa gagttggtag   3240
```

```
ctcttgatcc ggcaaacaaa ccaccgctgg tagcggtggt ttttttgttt gcaagcagca    3300
gattacgcgc agaaaaaaag gatctcaaga agatcctttg atcttttcta cggggtctga    3360
cgctcagtgg aacgaaaact cacgttaagg gattttggtc atgagattat caaaaaggat    3420
cttcacctag atccttttaa attaaaaatg aagttttaaa tcaatctaaa gtatatatga    3480
gtaaacttgg tctgacagtt accaatgctt aatcagtgag gcacctatct cagcgatctg    3540
tctatttcgt tcatccatag ttgcctgact ccccgtcgtg tagataacta cgatacggga    3600
gggcttacca tctggcccca gtgctgcaat gataccgcga acccacgct caccggctcc    3660 agatttatca gcaataaacc agccagccgg aagggccgag cgcagaagtg gtcctgcaac    3720
tttatccgcc tccatccagt ctattaattg ttgccgggaa gctagagtaa gtagttcgcc    3780
agttaatagt ttgcgcaacg ttgttgccat tgctacaggc atcgtggtgt cacgctcgtc    3840
gtttggtatg gcttcattca gctccggttc ccaacgatca aggcgagtta catgatcccc    3900
catgttgtgc aaaaaagcgg ttagctcctt cggtcctccg atcgttgtca gaagtaagtt    3960
ggccgcagtg ttatcactca tggttatggc agcactgcat aattctctta ctgtcatgcc    4020
atccgtaaga tgcttttctg tgactggtga gtactcaacc aagtcattct gagaatagtg    4080
tatgcggcga ccgagttgct cttgcccggc gtcaatacgg gataataccg cgccacatag    4140
cagaacttta aaagtgctca tcattggaaa acgttcttcg gggcgaaaac tctcaaggat    4200
cttaccgctg ttgagatcca gttcgatgta acccactcgt gcacccaact gatcttcagc    4260
atcttttact ttcaccagcg tttctgggtg agcaaaaaca ggaaggcaaa atgccgcaaa    4320
aaagggaata agggcgacac ggaaatgttg aatactcata ctcttccttt ttcaatatta    4380
ttgaagcatt tatcagggtt attgtctcat gagcggatac atatttgaat gtatttagaa    4440
aaataaacaa ataggggttc cgcgcacatt tccccgaaaa gtgccacctg acgtctaaga    4500
aaccattatt atcatgacat taacctataa aaataggcgt atcacgaggc cctttcgtct    4560
```

<210> SEQ ID NO 12  
<211> LENGTH: 386  
<212> TYPE: PRT  
<213> ORGANISM: Artificial Sequence  
<220> FEATURE:  
<223> OTHER INFORMATION: Bacteriophage against Virgibacillus sp.

<400> SEQUENCE: 12

```
Met Arg Gly Ser His His His His His His Gly Ser Met Gly Tyr Ile
  1               5                  10                  15

Ile Asp Ile Ser His His Gln Asp Pro Ala Lys Ile Asn Tyr Asp Lys
                 20                  25                  30

Leu Ala Lys Gln Val Asp Phe Ala Ile Ile Arg Thr Gln Tyr Gly Ser
             35                  40                  45

Arg Thr Leu Asp Ser His Tyr Lys Thr His His Gln Glu Leu Gln Lys
         50                  55                  60

Arg Gly Val Pro Thr Ala Ala Tyr Ala Trp Ile Arg Gly Val Ser Val
 65                  70                  75                  80

Asn Asp Met Glu Val Glu Ala Thr Asp Phe Tyr Asn Arg Thr Lys Glu
                 85                  90                  95

Phe Asn Pro Thr Phe Trp Phe Leu Asp Val Glu Glu Lys Ser Met Ser
                100                 105                 110

Asn Met Arg Lys Gly Ala Ser Ala Phe Leu Asn Lys Leu Arg Asp Leu
            115                 120                 125
```

-continued

```
Gly Ala Lys Lys Val Gly Ile Tyr Ile Ala Asn His Leu Tyr Asp Ser
    130                 135                 140

Phe Asn Ile Asp Val Asn Glu Ala Asp Ala Val Trp Ile Pro His Tyr
145                 150                 155                 160

Gly Ser Asn Asn Gly Lys Pro Asn Ser Lys Pro Asp His Pro Ala Asp
                165                 170                 175

Leu His Gln Tyr Thr Asp Arg Gly Arg Leu Asn Gly Tyr Ser Gly Asn
            180                 185                 190

Leu Asp Leu Asn Arg Ile Ile Ser Asp Glu Asp Leu Ser Tyr Phe Thr
        195                 200                 205

Asp Gly Gln Ala Thr Lys Lys Lys Thr Ser Ser Asn Lys Thr Ser Gly
    210                 215                 220

Ser Lys Ser Ser Asn Lys Ile Thr Gly Ser Thr Tyr Lys Val Lys Ser
225                 230                 235                 240

Gly Asp Thr Leu Ser Gly Ile Ala Ser Arg Ala Gly Thr Thr Thr Lys
                245                 250                 255

Asn Leu Gln Asp Ile Asn Asn Ile Ser Asn Pro Asp Leu Ile Lys Val
            260                 265                 270

Gly Gln Thr Ile Lys Leu Lys Gly Ser Ser Ser Asn Lys Thr Gly Gly
        275                 280                 285

Thr Thr Tyr Thr Val Lys Ser Gly Asp Thr Leu Ser Gly Ile Ala Ser
    290                 295                 300

Lys Phe Gly Thr Thr Thr Asn Lys Leu Gln Asp Leu Asn Gly Ile Ser
305                 310                 315                 320

Asn Pro Asp Lys Ile Tyr Ala Gly Gln Lys Ile Lys Val Ser Gly Ser
                325                 330                 335

Ser Ser Ser Lys Lys Tyr His Thr Val Lys Ser Gly Asp Thr Val Ser
            340                 345                 350

Glu Leu Ala Gln Gln Phe Gly Ser Asn Gln Ser Lys Ile Lys Ser Trp
        355                 360                 365

Asn Asn Leu Asp Ser Asn Tyr Thr Ile Tyr Val Gly Gln Lys Leu Arg
    370                 375                 380

Val Lys
385
```